US009365569B2

(12) United States Patent
Martos et al.

(10) Patent No.: US 9,365,569 B2
(45) Date of Patent: Jun. 14, 2016

(54) ANTAGONISTS ACTING AT MULTIPLE PROSTAGLANDIN RECEPTORS FOR THE TREATMENT OF INFLAMMATION

(71) Applicant: Allergan, Inc., Irvine, CA (US)

(72) Inventors: Jose L. Martos, Basildon Essex (GB); David F. Woodward, Lake Forest, CA (US); Jenny W. Wang, Irvine, CA (US); Steven Dabbs, Bishops Stortford (GB); Jussi J. Kangasmetsa, Cambridge (GB)

(73) Assignee: ALLERGAN, INC., Irvine, CA (US)

( * ) Notice: Subject to any disclaimer, the term of this patent is extended or adjusted under 35 U.S.C. 154(b) by 0 days.

(21) Appl. No.: 14/606,513

(22) Filed: Jan. 27, 2015

(65) Prior Publication Data

US 2015/0210689 A1  Jul. 30, 2015

Related U.S. Application Data

(60) Provisional application No. 61/931,756, filed on Jan. 27, 2014.

(51) Int. Cl.
*C07D 471/02* (2006.01)
*C07D 471/04* (2006.01)
*C07D 231/56* (2006.01)
*C07D 403/06* (2006.01)
*C07D 401/12* (2006.01)

(52) U.S. Cl.
CPC ............ *C07D 471/04* (2013.01); *C07D 231/56* (2013.01); *C07D 401/12* (2013.01); *C07D 403/06* (2013.01)

(58) Field of Classification Search
None
See application file for complete search history.

(56) References Cited

U.S. PATENT DOCUMENTS

| 4,166,452 | A | 9/1979 | Generales, Jr. |
| 4,256,108 | A | 3/1981 | Theeuwes |
| 4,265,874 | A | 5/1981 | Bonsen et al. |
| 6,511,999 | B2 | 1/2003 | Burk et al. |
| 8,494,424 | B2 | 7/2013 | Ishida et al. |
| 8,530,648 | B2 * | 9/2013 | Badiger ............... C07D 471/10 544/230 |
| 8,859,606 | B2 | 10/2014 | Woodward et al. |
| 2004/0162323 | A1 | 8/2004 | Krauss et al. |
| 2005/0065200 | A1 | 3/2005 | Woodward et al. |
| 2007/0060596 | A1 | 3/2007 | Giblin et al. |
| 2010/0093819 | A1 | 4/2010 | Morita et al. |

FOREIGN PATENT DOCUMENTS

| WO | 2008098978 | 8/2008 |
| WO | 2013096496 | 6/2013 |

OTHER PUBLICATIONS

Notification of Transmittal of the International Search Report and Written Opinion mailed on Mar. 5, 2015 for PCT/US2015/013119 filed on Jan. 27, 2015 in the name of Allergan, Inc.
Berge, S., et al., Pharmaceutical Salts, J. Pharma. Sci. 1977, 66: 1-19, 1.
Castellani, ML et al, Anti-Chemokine Therapy for Inflammatory Diseases, International Journal of Immunopathology and Pharmacology, 2007, 447-453, 20(3).
Conti, P. et al, MCP-1 and RANTES Are Mediators of Acute and Chronic Inflammation, Allergy and Asthma Proc, 2001, 133-137, 22.
Garcia, Gilles et al, New Chemokine Targets for Asthma Therapy, Current Allergy and Asthma Reports, 2005, 155-160, 5.
Gleissner, Christian A. et al, Platelet Chemokines in Vascular Disease, ATVB in Focus Chemokines in Atherosclerosis, Thrombosis, and Vascular Biology, 2008, 1920-1927, 28.
Ho, CY et al, Suppressive effect of combination treatment of leflunomide and methotrexate on chemokine expression in patients with rheumatoid arthritis, Clin Exp Immunol, 2003, 132-138, 133.
Iwamoto, Takuji et al, Molecular aspects of rheumatoid arthritis: chemokines in the joints of patients, The FEBS Journal, 2008, 4448-4455, 275.
Pivarcsi, Andor et al, Chemokine Networks in Atopic Dermatitis: Traffic Signals of Disease, Current Allergy and Asthma Reports, 2005, 284-290, 5.
Qi, Xu-Feng et al, The adenylyl cyclase-cAMP system suppresses TARC/CCL17 and MDC/CCL22 production through p38 MAPK and NF-KB in HaCaT keratinocytes, Molecular Immunology, 2009, 1925-1934, 46.
Remington's Pharmaceutical Sciences, Mack Publishing Company, 1980, 10 pgs, 16.
Remington's Pharmaceutical Sciences, Mack Publishing Company, 1985, 5 pgs, 17.

\* cited by examiner

*Primary Examiner* — Heidi Reese
(74) *Attorney, Agent, or Firm* — Jonathan Bass

(57) ABSTRACT

Compounds, processes for their preparation, pharmaceutical compositions containing such compounds and their use in treating therapeutic conditions, in particular conditions mediated by the action of ligands on the FP, DP, $EP_1$, $EP_4$, IP, $DP_1$, FP and TP prostaglandin (PG) receptors thereby providing a general anti-inflammatory response.

17 Claims, No Drawings

ANTAGONISTS ACTING AT MULTIPLE PROSTAGLANDIN RECEPTORS FOR THE TREATMENT OF INFLAMMATION

CROSS-REFERENCE TO RELATED APPLICATIONS

This application is a non-provisional application which claims the benefit of U.S. provisional application 61/931,756, entitled "Antagonists Acting At Multiple Prostaglandin Receptors For The Treatment Of Inflammation" and filed on Jan. 27, 2014, and which is incorporated by reference herein in its entirety and serves a basis for a benefit and/or priority claim for the present application.

FIELD OF THE INVENTION

This invention relates to compounds, processes for their preparation, pharmaceutical compositions containing such compounds and to their use in treating therapeutic conditions, in particular their use in the treatment of conditions mediated by the action of ligands for the FP, DP, $EP_1$, $EP_2$, $EP_3$, $EP_4$, IP, $DP_1$, FP and TP prostaglandin (PG) receptors. The present compounds, which in some embodiments can be antagonists, have the general structure as shown below and act at different prostaglandin receptors to thereby provide a general anti-inflammatory response.

BACKGROUND OF THE INVENTION

There are four G-protein-coupled receptors (GPCRs) which interact with the ligand prostaglandin $E_2$ which are designated subtypes $EP_1$, $EP_2$, $EP_3$ and $EP_4$. The $EP_1$ receptor is a 7-transmembrane receptor and its natural ligand is the prostaglandin $PGE_2$. $PGE_2$ also has affinity for the other EP receptors (types $EP_2$, $EP_3$ and $EP_4$). The $EP_1$ receptor is associated with smooth muscle contraction, pain (in particular inflammatory, neuropathic and visceral), inflammation, allergic activities, renal regulation and gastric or enteric mucus secretion.

Prostaglandin $E_2$ ($PGE_2$) exerts pain and pain related entities such as allodynia and hyperalgesia through the $EP_1$, $EP_4$ and $EP_3$ receptor subtypes (Woodward et al. Pharmacol Rev. 63: 471-538, 2011). Furthermore, it has been shown that in the $EP_1$ knockout mouse pain-sensitivity responses are reduced by approximately 50%. $EP_1$ receptor antagonist (ONO-8711) reduces hyperalgesia and allodynia in a rat model of chronic constriction injury and inhibits mechanical hyperalgesia in a rodent model of post-operative pain. The efficacy of $EP_1$ receptor antagonists in the treatment of visceral pain in a human model of hypersensitivity has been demonstrated. Thus, selective prostaglandin ligands depending on which prostaglandin EP receptor subtype is being considered, have anti-inflammatory, antipyretic and analgesic properties similar to a conventional non-steroidal anti-inflammatory drug, and in addition, inhibit hormone-induced uterine contractions and have anti-cancer effects. These compounds have a diminished ability to induce some of the mechanism-based side effects of NSAIDs which are indiscriminate cyclooxygenase inhibitors. In particular, the compounds have a reduced potential for gastrointestinal toxicity, a reduced potential for renal side effects, a reduced or absent potential for cardiovascular risk, a reduced effect on bleeding times and a lessened ability to induce asthma attacks in aspirin-sensitive asthmatic subjects. Moreover, as a result of sparing potentially beneficial prostaglandin pathways, these agents may have enhanced efficacy over NSAIDS and/or COX-2 inhibitors. (See Pub. No. US 2005/0065200, which is hereby incorporated by reference in its entirety, for other diseases that may be treated by $EP_4$ receptor antagonists).

The TP (also known as $TxA_2$) receptor is a prostanoid receptor subtype stimulated by the endogenous mediator thromboxane. Activation of this receptor results in various physiological actions primarily incurred by its platelet aggregatory and smooth muscle constricting effects, thus opposing those of prostacyclin receptor activation.

TP receptors have been identified in human kidneys in the glomerulus and extraglomerular vascular tissue. Activation of TP receptors constricts glomerular capillaries and suppresses glomerular filtration rates indicating that TP receptor antagonists could be useful for renal dysfunction in glomerulonephritis, diabetes mellitus and sepsis.

Activation of TP receptors induces bronchoconstriction, an increase in microvascular permeability, formation of mucosal edema and mucus secretion, which are typical characteristic features of bronchial asthma. TP antagonists have been investigated as potential asthma treatments resulting in, for example, orally active Seratrodast (AA-2414). Ramatroban is another TP receptor antagonist currently undergoing phase III clinical trials as an anti-asthmatic compound.

Since the $DP_1$ receptor may trigger an asthmatic response in certain individuals, compounds that have $DP_1$ antagonist properties may be useful as anti-asthmatic drugs. (See Pub. No. 2004/0162323, which is hereby incorporated by reference in its entirety, for the disclosure of other diseases and conditions that may be treated with DP antagonists.)

Finally, the FP receptor modulates intraocular pressure and mediates smooth muscle contraction of the sphincter muscles in the gastrointestinal tract and the uterus and contractile smooth muscle of these and other organs. Thus, antagonists of the FP receptor are useful for treating reproductive disorders. (See U.S. Pat. No. 6,511,999 which is hereby incorporated by reference in its entirety, for other diseases and conditions that may be treated with FP receptor antagonists.)

As further background for the present invention, see US Published Patent Application 2007/0060596, U.S. Pat. No. 8,494,424 and U.S. application Ser. No. 13/746,023, all of which are hereby incorporated by reference in their entireties.

SUMMARY OF THE INVENTION

In one aspect, this present invention is directed to compounds of formula I:

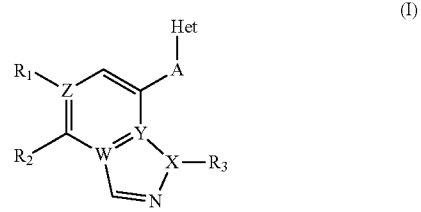

wherein:
  A is selected from the group consisting of $C_1$-$C_3$ alkylene and CO;

X is either CH or N, wherein:
  when X is CH, $R_3$ is selected from the group consisting of:

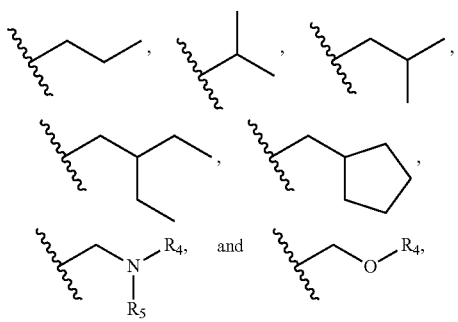

and when X is N, $R_3$ is selected from the group consisting of:

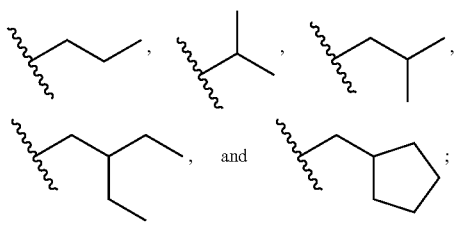

W and Y are either C or N;
Z is either C or N, wherein:
  when Z is C, $R_1$ is selected from the group consisting of $C_1$-$C_3$ alkyl, $C_1$-$C_3$ haloalkyl, $CH_2OCH_3$, F, Cl, Br, halogen, $OCF_3$, $OCCl_3$, $OCBr_3$ and wherein $C_1$-$C_3$ alkyl may be optionally substituted by hydroxyl, halogen, amine and functional amines,
  and when Z is N, there is no $R_1$ substituent;
$R_2$ is selected from the group consisting of H, $C_1$-$C_3$ alkyl, $C_1$-$C_3$ haloalkyl, $CH_2OCH_3$, F, Cl, Br, halogen, and $OCF_3$;
$R_4$ and $R_5$ are independently selected from the group consisting of $C_1$-$C_3$ alkyl and substituted $C_1$-$C_3$ alkyl, and when $R_3$ is

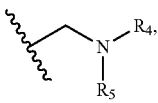

$R_4$ and $R_5$ can be joined to form a $C_3$-$C_6$ cycloalkyl;
Het is selected from the group consisting of:

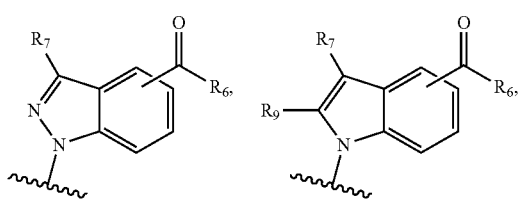

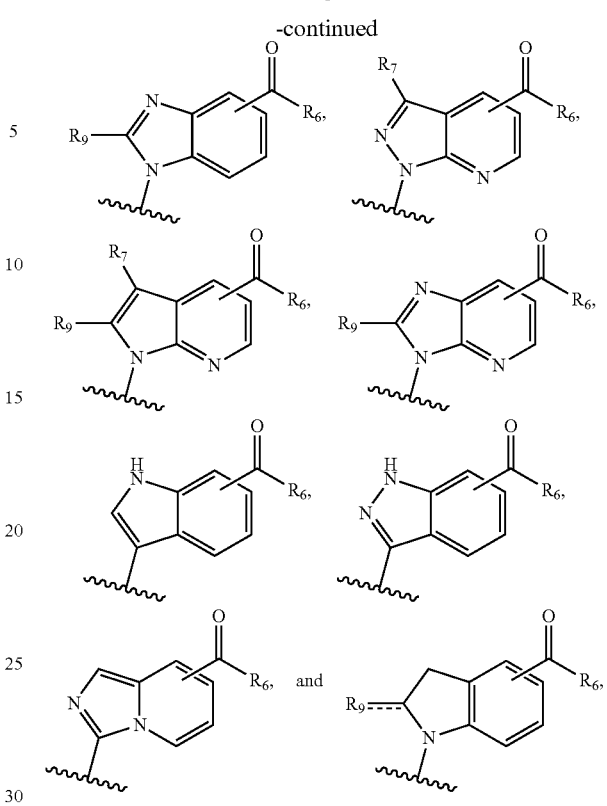

wherein:
  $R_6$ is selected from the group consisting of OH, $OCH_3$, $OCH(CH_3)_2$, and $NHSO_2R_8$;
  $R_7$ is selected from the group consisting of H, $CH_3$, $CH_2CH_3$, $OCH_3$, $CH_2OH$, $CH_2OCH_3$, $NH_2$, $C_1$-$C_3$ alkylamino, and $C_1$-$C_3$ dialkylamino;
  $R_8$ is selected form the group consisting of $C_1$-$C_3$ alkyl and substituted $C_1$-$C_3$ alkyl; and,
  $R_9$ is selected from the group consisting of 0, OH, $CH_3$, halogen and $OCH_3$ the dashed bond represents the presence of a single or double bond;
  and wherein the compounds can be in the form of a tautomer, a racemate, an enantiomer, a diastereomer, or a pharmaceutically acceptable salt.

In some embodiments, A can be $C_1$-$C_3$ alkylene, CO or $CH_2$.
In some embodiments, Z can be C.
In some embodiments, X can be N.
In some embodiments, $R_3$ can be selected from group consisting of:

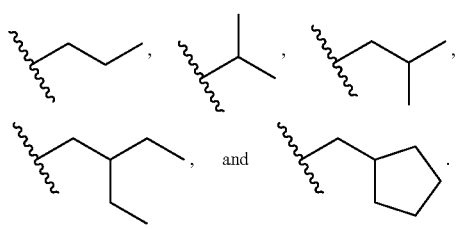

In some embodiments, $R_1$ can be halogen and $R_2$ can be H.

In some embodiments, Het can be selected from the group consisting of:

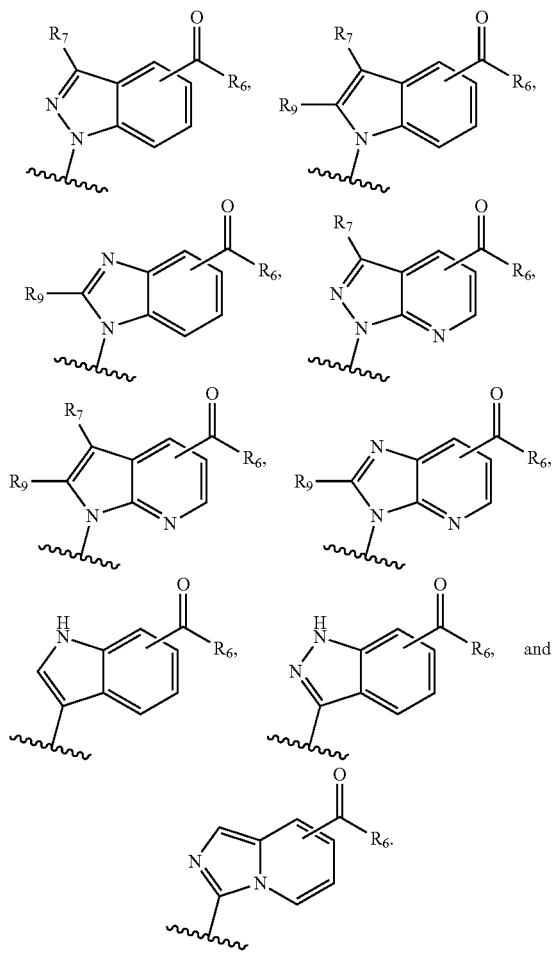

In some embodiments, Het can be:

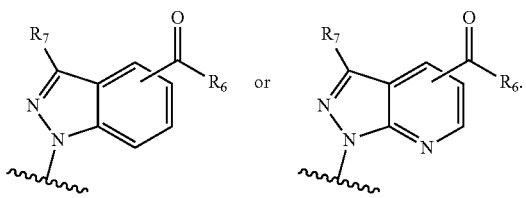

In some embodiments, Z is C, $R_1$ is Cl or Br, and $R_7$ is H or $NHCH_3$.

In some embodiments, X is N, $R_6$ is OH and $R_3$ is:

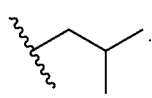 [SMILES: *CC(C)C]

In another aspect, the invention is directed to a compound selected from the group consisting of:

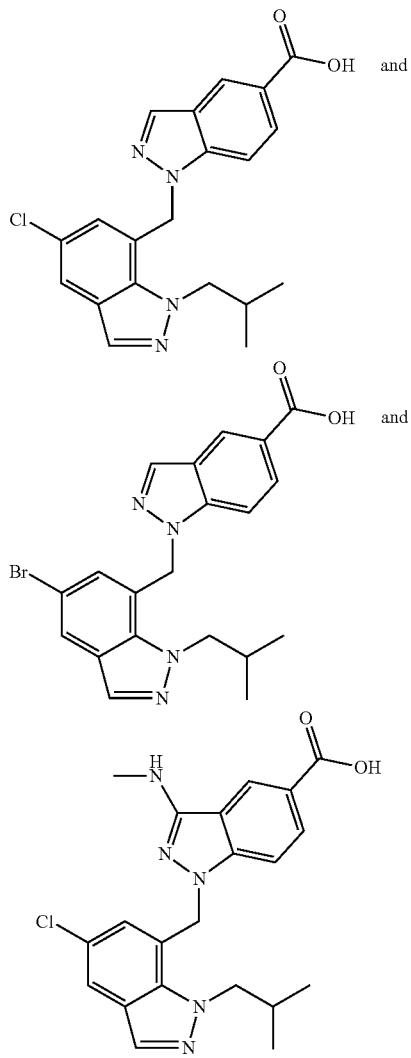

or a pharmaceutically acceptable salt thereof

In another aspect, the invention is directed to a compound of general formula I as described herein, for use as an antagonist for a prostanoid receptor, or for use in the treatment of a condition mediated by prostanoid receptors.

In another aspect, the invention is directed to a compound of general formula I as described herein, for use in the treatment of a condition mediated by an $EP_1$ receptor.

In another aspect, the invention is directed to a compound of general formula I as described herein, for use in the treatment of a condition mediated by an $EP_4$ receptor.

In another aspect, the invention is directed to a method of treating a human suffering from a therapeutic condition mediated by prostanoid receptors, the method comprising administering an effective amount of a compound according to general formula I as described herein.

A method of treating a patient suffering from a condition selected from the group consisting of inflammatory pain, neuropathic pain, visceral pain, fibrosis and a condition of the central nervous system mediated by prostanoid receptors, the method comprises administering to said patient an effective amount of a compound of general formula 1.

Some embodiments of the present invention are included in the following paragraphs:

1. A compound of formula (I):

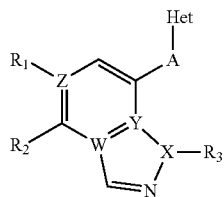

wherein:

A is selected from the group consisting of $C_1$-$C_3$ alkylene and CO;

X is either CH or N, wherein:
when X is CH, $R_3$ is selected from the group consisting of:

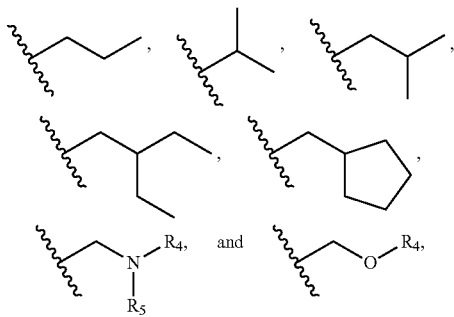

and when X is N, $R_3$ is selected from the group consisting of:

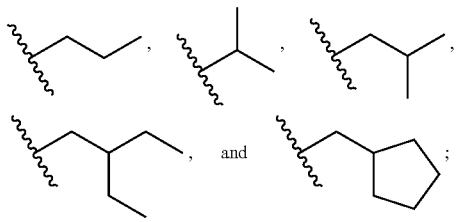

W and Y are either C or N;

Z is either C or N, wherein:
when Z is C, $R_1$ is selected from the group consisting of $C_1$-$C_3$ alkyl, $C_1$-$C_3$ haloalkyl, $CH_2OCH_3$, F, Cl, Br, halogen, $OCF_3$, $OCCl_3$, $OCBr_3$ and wherein $C_1$-$C_3$ alkyl may be optionally substituted by hydroxyl, halogen, amine and functional amines, and when Z is N, there is no $R_1$ substituent;

$R_2$ is selected from the group consisting of H, $C_1$-$C_3$ alkyl, $C_1$-$C_3$ haloalkyl, $CH_2OCH_3$, F, Cl, Br, halogen, and $OCF_3$;

$R_4$ and $R_5$ are independently selected from the group consisting of $C_1$-$C_3$ alkyl and substituted $C_1$-$C_3$ alkyl, and when $R_3$ is

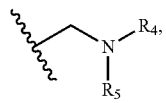

$R_4$ and $R_5$ can be joined to form a $C_3$-$C_6$ cycloalkyl;

Het is selected from the group consisting of:

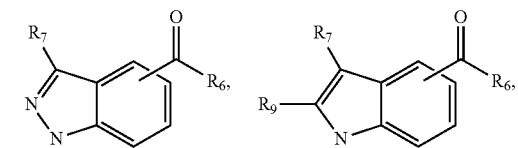

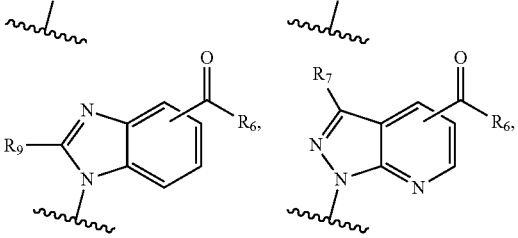

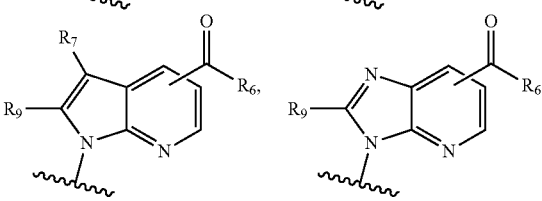

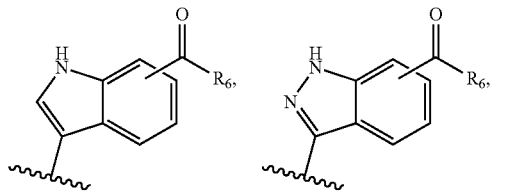

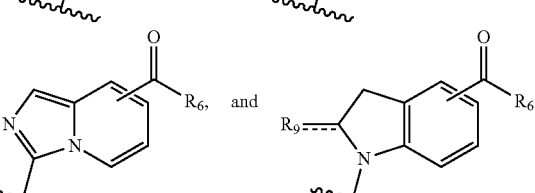

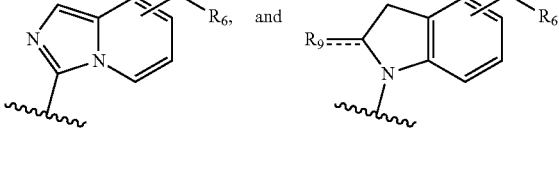

wherein:
$R_6$ is selected from the group consisting of OH, $OCH_3$, $OCH(CH_3)_2$, and $NHSO_2R_8$;

$R_7$ is selected from the group consisting of H, $CH_3$, $CH_2CH_3$, $OCH_3$, $CH_2OH$, $CH_2OCH_3$, $NH_2$, $C_1$-$C_3$ alkylamino, and $C_1$-$C_3$ dialkylamino;

$R_8$ is selected form the group consisting of $C_1$-$C_3$ alkyl and substituted $C_1$-$C_3$ alkyl; and, $R_9$ is selected from the group consisting of 0, OH, $CH_3$, halogen and $OCH_3$ the dashed bond represents the presence of a single or double bond;

and wherein the compounds may be in the form of a tautomer, a racemate, an enantiomer, a diastereomer, or a pharmaceutically acceptable salt.

2. The compound of paragraph 1, wherein A is $C_1$-$C_3$ alkyl.

3. The compound of paragraph 1, wherein A is CO.

4. The compound of paragraphs 1 or 2, wherein A is selected from the group consisting of $CH_2$, $CH_2CH$ or $CH_2CH_2CH_2$.

5. The compound of paragraphs 1-4, wherein Z is C and X is N.

6. The compound of paragraph 5, wherein $R_3$ is selected from group consisting of:

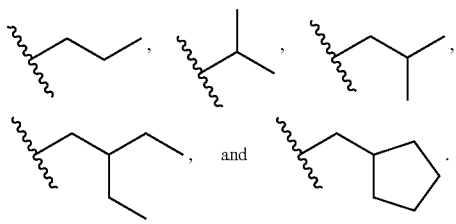

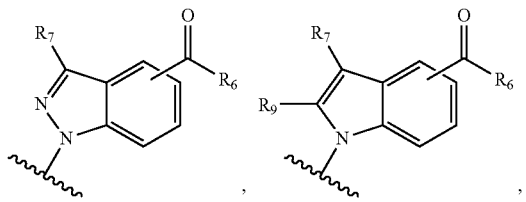

7. The compound of paragraphs 1 to 6, where $R_1$ is halogen.
8. The compound of paragraphs 1 to 6, wherein $R_2$ is H.
9. The compound of paragraphs 1 to 8, wherein Het is selected from the group consisting of:

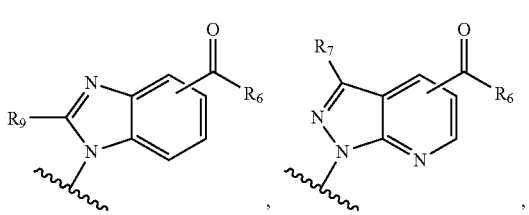

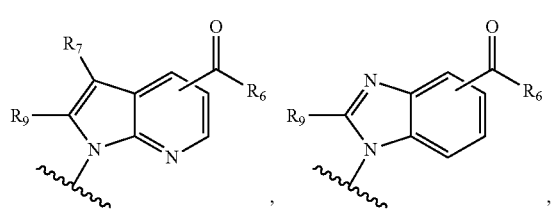

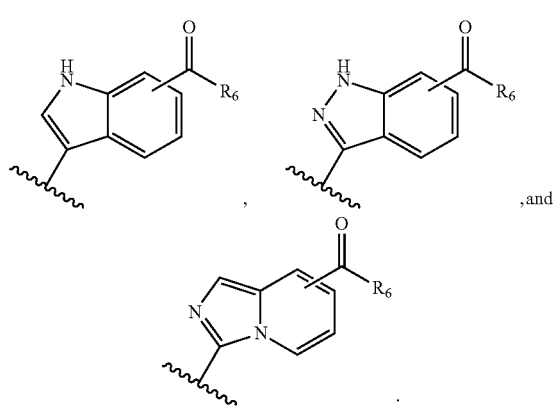

10. The compound of paragraph 9, wherein Het is

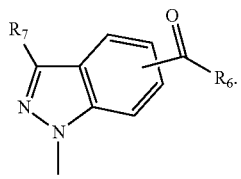

11. The compound of paragraph 9 wherein Het is selected from the group consisting of

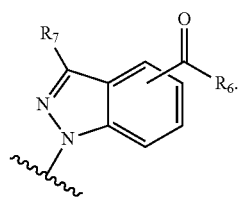

12. The compound of paragraph 1 wherein Z is C, $R_1$ is Cl or Br and $R_7$ is H or $NCH_3$.

13. The compound of paragraph 12 wherein X is N, $R_6$ is OH and $R_3$ is

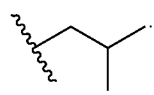

14. The compound of paragraph 13 selected from the group consisting of

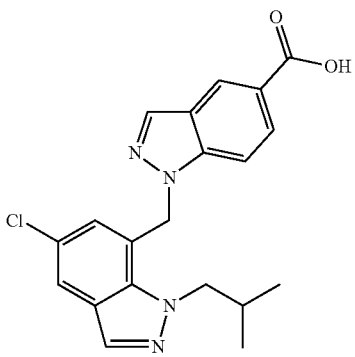

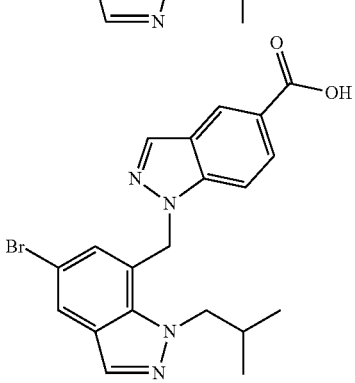

-continued

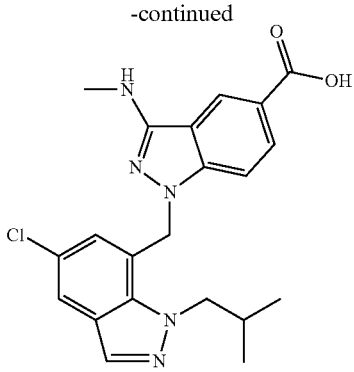

or a pharmaceutical acceptable salt thereof.

15. The compound of paragraph 1 selected from the group consisting of:
1-(5-Chloro-1-isobutyl-1H-indazol-7-ylmethyl)-1H-indazole-5-carboxylic acid;
1-(5-Bromo-1-isobutyl-1H-indazol-7-ylmethyl)-1H-indazole-5-carboxylic acid;
1-(5-Fluoro-1-isobutyl-1H-indazol-7-ylmethyl)-1H-indazole-5-carboxylic acid;
1-(1-Isobutyl-5-trifluoromethyl-1H-indazol-7-ylmethyl)-1H-indazole-5-carboxylic acid;
1-(1-Isobutyl-5-trifluoromethoxy-1H-indazol-7-ylmethyl)-1H-indazole-5-carboxylic acid;
1-(5-Bromo-1-isopropyl-1H-indazol-7-ylmethyl)-1H-indazole-5-carboxylic acid;
1-[5-Bromo-1-(2-ethyl-butyl)-1H-indazol-7-ylmethyl]-1H-indazole-5-carboxylic acid;
1-[5-Chloro-1-(2-propyl)-1H-indazol-7-ylmethyl]-1H-indazole-5-carboxylic acid;
1-(5-Chloro-1-isobutyl-1H-indazol-7-ylmethyl)-1H-pyrazolo[3,4-b]pyridine-5-carboxylic acid;
1-(5-Chloro-1-isobutyl-1H-indazol-7-ylmethyl)-1H-benzoimidazole-5-carboxylic acid;
3-(5-Chloro-1-isobutyl-1H-indazol-7-ylmethyl)-3H-imidazo[4,5-b]pyridine-6-carboxylic acid;
1-(5-Chloro-1-isobutyl-1H-indazol-7-ylmethyl)-1H-pyrrolo[2,3-b]pyridine-5-carboxylic acid;
1-(5-Bromo-1-isobutyl-1H-indazol-7-ylmethyl)-3-methyl-1H-indazole-5-carboxylic acid;
1-(5-Bromo-1-isobutyl-1H-indazol-7-ylmethyl)-3-methyl-1H-pyrazolo[3,4-b]pyridine-5-carboxylic HCl salt;
1-(1-Isobutyl-5-trifluoromethyl-1H-indazol-7-ylmethyl)-1H-benzoimidazole-5-carboxylic acid;
1-(1-Isobutyl-5-trifluoromethoxy-1H-indazol-7-ylmethyl)-1H-benzoimidazole-5-carboxylic acid;
3-[(5-Chloro-1-isobutyl-indazol-7-yl)methyl]imidazo[1,5-a]pyridine-7-carboxylic acid;
1-(5-Chloro-1-isobutyl-1H-indazol-7-ylmethyl)-2-oxo-2,3-dihydro-1H-indole-5-carboxylic acid;
3-Amino-1-[(5-chloro-1-isobutyl-indazol-7-yl)methyl]indazole-5-carboxylic acid;
1-[(5-Chloro-1-isobutyl-indazol-7-yl)methyl]-3-(methylamino)indazole-5-carboxylic acid
or a pharmaceutically acceptable salt thereof.

15. The compound of paragraph 1, for use as an antagonist for a prostanoid receptor.

16. The compound of paragraph 1, for use in the treatment of a condition mediated by prostanoid receptors.

17. The compound of paragraph 14, for use in the treatment of a condition mediated by an $EP_1$ receptor.

18. The compound of paragraph 14, for use in the treatment of a condition mediated by an $EP_4$ receptor.

19. A method of treating a human suffering from a therapeutic condition mediated by prostanoid receptors, the method comprising administering an effective amount of a compound according to paragraph 1.

20. A method of treating a patient suffering from a condition selected from the group consisting of inflammatory pain, neuropathic pain, visceral pain, fibrosis and a condition of the central nervous system mediated by prostanoid receptors, the method comprises administering to said patient an effective amount of a compound of paragraph 1.

21. The compound of paragraph 1 wherein:
A is $CH_2$;
$R_1$ is selected from the group consisting of F, $CF_3$, Cl, Br, halogen, and $OCF_3$;
$R_2$ is selected from H, Cl, Br and $OCF_3$;
$R_3$ is selected from the group consisting of:

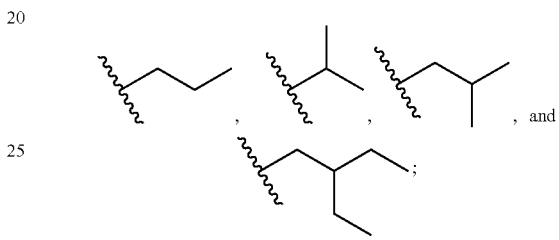

, and

Het is selected from the group consisting of:

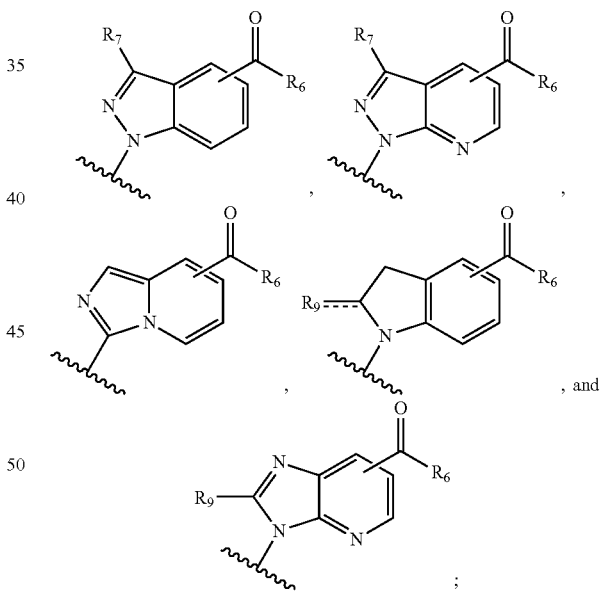

, and wherein $R_6$ is selected from the group consisting of OH and $OCH_3$,
wherein $R_7$ is selected from the group consisting of H, $CH_3$, $NH_2$ and $NHCH_3$,
wherein $R_9$ is O, OH, $CH_3$, halogen and $OCH_3$ the dashed bond represents the presence of a single or double bond,
and, the compound can be in the form of a tautomer, a racemate, an enantiomer, a diastereomer, or a pharmaceutically acceptable salt.

22. The compound of paragraph 21 wherein W and Y are C, $R_1$ is selected from Cl, Br, F, $CF_3$, and $OCF_3$.

23. The compound of paragraphs 21 and 22 wherein Het is:

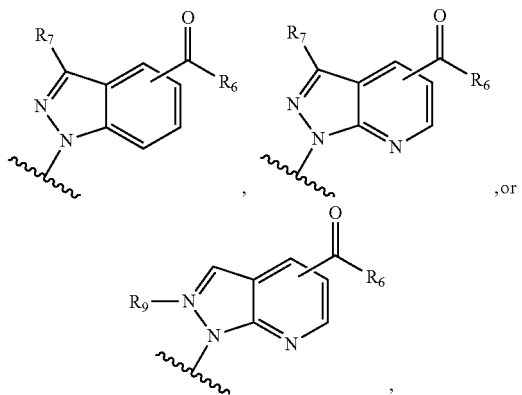

wherein $R_6$ is OH, wherein $R_7$ is selected from the group consisting of H, $CH_3$, $NH_2$ and $NHCH_3$, wherein $R_9$ is O, OH, $CH_3$, halogen and $OCH_3$ the dashed bond represents the presence of a single or double bond, and, the compounds can be in the form of a tautomer, a racemate, an enantiomer, a diastereomer, or a pharmaceutically acceptable salt.

DETAILED DESCRIPTION OF THE INVENTION

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

Where substituents are specified as a range, the range encompasses each individual integer value of substituent including the beginning and ending value of the range. For example, the description of a substituent as "$C_1$ to $C_6$ alkyl" (or "$C_1$-$C_6$ alkyl") encompasses $C_1$ alkyl, $C_2$ alkyl, $C_3$ alkyl, $C_4$ alkyl, $C_5$ alkyl, and $C_6$ alkyl. Similarly, the description of a value of "n" (e.g. "$(CH_2)_n$") as being "0 to 3" (or "0-3") encompasses values of "n" of 0, 1, 2, and 3. A skilled person will realize upon a reading of the present disclosure that similar considerations apply to other substituents that can be described in terms of a range (e.g. "5 to 10 ring atoms" and "1 to 3 rings").

The term "acyl" means —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl or substituted or unsubstituted heteroaryl.

The term "alkyl," by itself or as part of another substituent, means, unless otherwise stated, a straight (i.e. unbranched) or branched chain, or combination thereof, which may be fully saturated (referred to herein as a "saturated alkyl"), mono- or polyunsaturated and can include di- and multivalent radicals, having the number of carbon atoms designated (i.e. $C_1$-$C_{10}$ means one to ten carbons). Typical alkyl groups include methyl, ethyl, propyl, isopropyl, butyl, isobutyl, tertiary butyl, pentyl, hexyl and the like. In some embodiments, all alkyls set forth as a substituent of the compounds provided herein are saturated alkyls. Examples of saturated hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated alkyl group is one having one or more double bonds or triple bonds. An "alkoxy" is an alkyl attached to the remainder of the molecule via an oxygen linker (—O—). An "alkylthio" is an alkyl attached to the remainder of the molecule via an sulfur linker (—S—). A "haloalkoxy" is an alkoxy substituted with a halogen. When the halogen is a fluoro, it may be referred to herein as a "fluoroalkoxy." The term "alkyl" includes saturated alkyl, alkenyl and alkynyl. A saturated alkyl may have from 1 to 10 or 1 to 6 carbon atoms. The term "alkenyl" by itself or as part of another substituent, means, unless otherwise stated, a straight (i.e. unbranched) or branched hydrocarbon chain (e.g., two to ten, or two to six carbon atoms) having one or more double bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), and the like. The term "alkynyl" by itself or as part of another substituent, means, unless otherwise stated, a straight (i.e. unbranched) or branched hydrocarbon chain (e.g., two to ten or two to six carbon atoms) having one or more triple bonds. Examples of alkynyl groups include, but are not limited to, ethynyl, 1- and 3-propynyl, 3-butynyl, and the like.

The term "alkylene", "alkenylene, and "alkynylene" by itself or as part of another substituent means a divalent radical derived from an alkyl, alkenyl, or alkynyl as exemplified, but not limited, by methylene, ethylene, —$CH_2CH_2CH_2CH_2$—, vinylene and the like.

"Alkylenyl" refers to a divalent alkyl linking group.

The term "amino" as used herein means a —$NH_2$. The term "carboxy" as used herein means —COOH (including pharmaceutically acceptable salts thereof).

The term "aryl" means, unless otherwise stated, an aromatic substituent of 3 to 14 atoms (e.g. 6 to 10) which can be a single ring or multiple rings (e.g., from 1 to 3 rings) which may be fused together (i.e. a fused ring aryl) or linked covalently. A fused ring aryl refers to multiple rings fused together wherein at least one of the fused rings is an aryl ring (e.g., phenyl, 1-naphthyl, 2-naphthyl, or 4-biphenyl). The term "heteroaryl" refers to aryl groups (or rings) that contain one or more (e.g., 4) heteroatoms selected from N, O, and S, wherein the nitrogen and sulfur atoms are optionally oxidized, and the nitrogen atom(s) are optionally quaternized, the remaining ring atoms being carbon. The heteroaryl may be a monovalent monocyclic, bicyclic, or tricyclic (e.g., monocyclic or bicyclic) aromatic radical of 5 to 14 (e.g., 5 to 10) ring atoms where one or more, (e.g., one, two, or three or four) ring atoms are heteroatom selected from N, O, or S. Examples include, but are not limited to, thienyl, isoindolyl, benzoxazolyl, pyridazinyl, triazolyl, tetrazolyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidinyl, 4-pyrimidinyl, 5-benzothiazolyl, 2-benzimidazolyl, 5-indolyl, 1-isoquinolyl, 5-isoquinolyl, 2-quinoxalinyl, 5-quinoxalinyl, 3-quinolyl, and 6-quinolyl. Thus, the term "heteroaryl" includes fused ring heteroaryl groups (i.e. multiple rings fused together wherein at least one of the fused rings is a heteroaromatic ring). A 5.6-fused ring heteroaryl refers to two rings fused together, wherein one ring has 5 members and the other ring has 6 members, and wherein at least one ring is a heteroaryl ring. Likewise, a 6.6-fused ring heteroaryl refers to two rings fused together, wherein one ring has 6 members and the other ring has 6 members, and wherein at least one ring is a heteroaryl ring. And a 6.5-fused ring heteroaryl refers to two rings fused together, wherein one ring has 6 members and the other ring has 5 members, and wherein at least one ring is a heteroaryl ring. A heteroaryl group can be attached to the remainder of the molecule through a carbon or heteroatom. An "arylene" and a "heteroarylene," alone or as part of another substituent means a divalent radical derived from an aryl and heteroaryl, respectively.

The terms "arylalkyl" and "heteroarylalkyl" is meant to include those radicals in which an aryl group or a heteroaryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "Ethylenyl" refers to a —CH$_2$CH$_2$— linking group.

The term "heteroalkyl," by itself or in combination with another term, means, unless otherwise stated, a stable straight or branched chain or combinations thereof, consisting of at least one carbon atom and at least one heteroatom selected from the group consisting of O, N, P, Si or S, and wherein the nitrogen and sulfur atoms may optionally be oxidized and the nitrogen heteroatom may optionally be quaternized. The heteroatom(s) O, N, P and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two heteroatoms may be consecutive, such as, for example, —CH$_2$—NH—OCH$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). As described above, heteroalkyl groups, as used herein, include those groups that are attached to the remainder of the molecule through a heteroatom The terms "cycloalkyl" and "heterocycloalkyl," by themselves or in combination with other terms, represent, unless otherwise stated, non-aromatic cyclic versions of "alkyl" and "heteroalkyl", respectively (e.g., having 4 to 8 ring atoms). Additionally, for heterocycloalkyl, a heteroatom can occupy the position at which the heterocycle is attached to the remainder of the molecule. Heterocycloalkyls may include one or two ring heteroatoms selected from N, O, or S(O)$_{n'}$, where n' is an integer from 0 to 2, the remaining ring atoms being carbon. The heterocycloalkyl or cycloalkyl ring is optionally fused to one or more aryl or heteroaryl rings as defined herein (e.g., where the aryl and heteroaryl rings are monocyclic). The heterocycloalkyl or cycloalkyl ring fused to monocyclic aryl or heteroaryl ring may be referred to in this Application as "bicyclic heterocycloalkyl" ring or a "bicyclic cycloalkyl" ring. Additionally, one or two ring carbon atoms in the heterocycloalkyl ring can optionally be replaced by a —CO— group. More specifically the term heterocycloalkyl includes, but is not limited to, pyrrolidino, piperidino, homopiperidino, 2-oxopyrrolidinyl, 2-oxopiperidinyl, morpholino, piperazino, tetrahydropyranyl, thiomorpholino, dihydroindolyl, and the like. When the heterocycloalkyl ring is unsaturated it can contain one or two ring double bonds provided that the ring is not aromatic. When the heterocycloalkyl group contains at least one nitrogen atom, it may also be referred to herein as heterocycloamino and is a subset of the heterocycloalkyl group. When the heterocycloalkyl group is a saturated ring and is not fused to aryl or heteroaryl ring as stated above, it may be referred to herein as a saturated monocyclic heterocycloalkyl. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent means a divalent radical derived from a cycloalkyl and heterocycloalkyl, respectively; C1-C3 alkyl includes methyl, ethyl and propyl.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is meant to include, but not be limited to, fluoromethyl, difluoromethyl, trifluoromethyl, 2,2,2-trifluoroethyl, 4-chlorobutyl, 3-bromopropyl, and the like.

The term "methylenyl" refers to a —CH$_2$— linking group.

The term "oxo" as used herein means an oxygen that is double bonded to a carbon atom. The term "carbonyl" as used herein refers to a —C(O)— group.

The symbol "〰" indicates, as is customary in the art, the point of attachment of a substituent.

The terms "optional" or "optionally" means that the subsequently described event or circumstance may but need not occur, and that the description includes instances where the event or circumstance occurs and instances in which it does not. For example, "heterocycloalkyl group optionally substituted with an alkyl group" means that the alkyl may but need not be present, and the description includes situations where the heterocycloalkyl group is substituted with an alkyl group and situations where the heterocycloalkyl group is not substituted with alkyl.

Each of the above terms (e.g., "alkyl," "heteroalkyl," "aryl" and "heteroaryl") are meant to include both substituted and unsubstituted forms of the indicated radical unless stated otherwise.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR'—C(NR'R"R''')=NR"", —NR—C(NR' R")=NR"", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R''' and R"" each independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —$C(O)CH_3$, —$C(O)CF_3$, —$C(O)CH_2OCH_3$, and the like).

Similar to the substituents described for the alkyl radical, substituents for the aryl and heteroaryl groups are varied and may be selected from, for example: halogen, —OR', —NR'R", —SR', -halogen, —SiR'R"R'", —OC(O)R', —C(O)R', —$CO_2$R', —CONR' R", —OC(O)NR'R", —NR"C(O)R', —NR'—C(O)NR'R", —NR"C(O)$_2$R', —NR—C(NR'R"R'")=NR"", —NR'—C(NR'R")=NR'", —S(O)R', —S(O)$_2$R', —S(O)$_2$NR'R", —NR'SO$_2$R', —CN and —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

Unless otherwise stated, the term "heteroatom" or "ring heteroatom" is meant to include oxygen (O), nitrogen (N), sulfur (S), phosphorus (P), and silicon (Si).

A "substituent group," as used herein, means, but is not limited to, a group selected from the following moieties:

(A) —OH, —$NH_2$, —SH, —CN, —$CF_3$, —$NO_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "lower substituent" or "lower substituent group," as used herein means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

Unless otherwise stated, structures depicted herein are also meant to include all stereochemical forms of the structure; e.g., the R and S configurations for each asymmetric center as well as cis and trans configurations. Therefore, single stereochemical isomers as well as enantiomeric and diastereomeric mixtures of the present compounds are within the scope of the invention.

The compounds of the present invention may have asymmetric centers and/or geometric isomers. Compounds of the present invention containing an asymmetrically substituted atom may be isolated in optically active or racemic forms. It is well known in the art how to prepare optically active forms, such as by resolution of materials. All chiral, diastereomeric, racemic forms are within the scope of this invention, unless the specific stereochemistry or isomeric form is specifically indicated. All possible tautomers and cis and trans isomers, as individual forms and mixtures thereof are within the scope of this invention. Additionally, as used herein the term alkyl includes all the possible isomeric forms of the alkyl group albeit only a few examples are set forth. Furthermore, when the cyclic groups such as aryl, heteroaryl, heterocycloalkyl are substituted, they include all the positional isomers albeit only a few examples are set forth. Furthermore, all polymorphic forms, including amorphous form, and hydrates of a compound disclosed herein are within the scope of this invention.

Certain compounds of the present invention possess asymmetric carbon atoms (optical centers) or double bonds; the racemates, diastereomers, tautomers, geometric isomers and individual isomers are encompassed within the scope of the present invention, as are enantiomers. The compounds of the present invention do not include those which are known in the art to be too unstable to synthesize and/or isolate.

Certain compounds of the present invention can exist as tautomers which can interconvert between themselves. The structural depiction herein of a particular tautomer should not be construed as limiting the compound to the particular tautomer depicted. By way of example, 2-hydroxybenzimidazoles can exist as, and interconvert between, a hydroxy or keto tautomer:

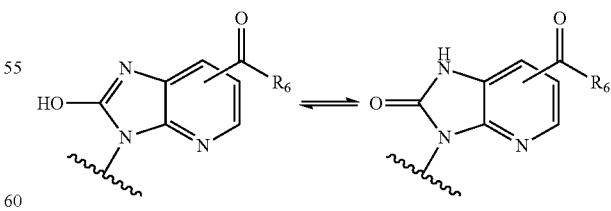

A skilled person will realize upon reading the present disclosure that the structural depiction of a compound of the present invention comprising a 2-hydroxybenzimidazole moiety as the hydroxy tautomer should not be construed as being limited to only the hydroxy tautomer and should be construed as including the keto tautomer even if the depicted hydoxy tautomer is the minor component in the tautomer interconversion equilibrium under a particular set of conditions. A skilled person will realize that similar considerations apply to other moieties (e.g. heterocycles) of the present invention that are capable of existing as different tautomers.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl.

Unless indicated otherwise, the term "derivative" in the context of a compound disclosed herein refers to a compound afforded by chemical modification, e.g., by the bonding of one or more substituent groups as described herein.

Where a moiety is substituted with an R substituent, the group may be referred to as "R-substituted." Where a moiety is R-substituted, the moiety is substituted with at least one R substituent and each R substituent is optionally different. For example, where a moiety herein is $R^{14}$-substituted or unsubstituted alkyl, a plurality of $R^{14}$ substituents may be attached to the alkyl moiety wherein each $R^{14}$ substituent is optionally different. Where an R-substituted moiety is substituted with a plurality R substituents, each of the R-substituents may be differentiated herein using a prime symbol (') such as R', R", etc. For example, where a moiety is $R^{14}$-substituted or unsubstituted alkyl, and the moiety is substituted with a plurality of $R^{14}$ substituents, the plurality of $R^{14}$ substituents may be differentiated as $R^{14'}$, $R^{14''}$, $R^{14'''}$, etc. In some embodiments, the plurality of R substituents is 3. In some embodiments, the plurality of R substituents is 2.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like. See e.g., Berge et al., "Pharmaceutical Salts", *Journal of Pharmaceutical Science,* 1977, 66, 1-19). Additional information on suitable pharmaceutically acceptable salts can be found in REMINGTON'S PHARMACEUTICAL SCIENCES, 17th ed., Mack Publishing Company, Easton, Pa., 1985, which is incorporated herein by reference. Certain specific compounds of the present invention contain both basic and acidic functionalities that allow the compounds to be converted into either base or acid addition salts.

Thus, the compounds disclosed herein may exist as salts. Examples of such salts include hydrochlorides, hydrobromides, sulfates, methanesulfonates, nitrates, maleates, acetates, citrates, fumarates, tartrates (e.g., (+)-tartrates, (−)-tartrates or mixtures thereof including racemic mixtures), succinates, benzoates and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

The term "prodrug" is used according to its plain ordinary meaning and is intended to mean compounds that require a chemical or enzymatic transformation in order to release the active parent drug in vivo prior to producing a pharmacological effect.

A "pharmaceutically acceptable carrier" or "pharmaceutically acceptable excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

The terms "treat" "treating" or "treatment" refers to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the certain methods presented herein successfully treat cancer by decreasing the incidence of cancer, in inhibiting its growth and or causing remission of cancer.

An "effective amount" of a compound is an amount sufficient to contribute to the treatment, prevention, or reduction of a symptom or symptoms of a disease. Where recited in reference to a disease treatment, an "effective amount" may also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of a disease, disorder or condition, or reducing the likelihood of the onset (or reoccurrence) of a disease, disorder or condition or symptoms thereof. The full prophylactic effect does not necessarily occur by administration of one dose, and may occur only after administration of a series of doses. Thus, a prophylactically effective amount may be administered in one or more administrations.

The term "topical" in the context of methods described herein relates in the customary sense to the administration of a compound or pharmaceutical composition which is incorporated into a suitable pharmaceutical carrier and administered at a topical treatment site of a subject. Accordingly, the term "topical pharmaceutical composition" includes those pharmaceutical forms in which the compound is administered externally by direct contact with a topical treatment site, e.g., the eye or the skin. The term "topical ocular pharmaceutical composition" refers to a pharmaceutical composition suitable for administering directly to the eye. The term "topical epidermal pharmaceutical composition" refers to a pharmaceutical composition suitable for administering directed to the epidermal layer of the skin, e.g., the palpebra, the supercilium, the scalp, or the body. The term "topical administering" refers to administering externally by direct contact with a topical treatment site. The term "topical epidermal administering" refers to administering externally by direct contact with the epidermis. The term "topical ocular administering" refers to administering externally by direct contact with the eye.

EXAMPLES

The following examples are for illustrative purposes only and are not intended, nor should they be construed as limiting the invention in any manner. Those skilled in the art will appreciate that variations and modifications of the following examples can be made without exceeding the spirit or scope of the invention.

Example 1

Methyl 2-amino-5-(trifluoromethyl)benzoate, Compound 1

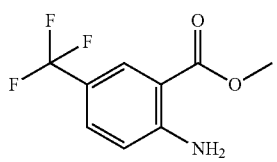

A solution of 2-amino-5-(trifluoromethyl)benzoic acid (1.07 g, 5.2 mmoles) in methanol (20 ml) was treated with concentrated sulphuric acid (0.5 ml) and heated under microwave conditions at 125° C. for 2 h. The mixture was evaporated to dryness and treated with water (100 ml) then basified to saturation with potassium carbonate and extracted with ethyl acetate (2×40 ml). The combined extracts were dried over sodium sulphate, filtered and evaporated to dryness. The residue was chromatographed on silica gel eluting with an ethyl acetate/isohexane gradient. This gave the title compound 1 as a colorless oil (0.59 g, 51%).

$^1$H-NMR (CDCl$_3$, 300 MHz) δ 8.15 (s, 1H, ArH), 7.47 (dd, J=2 and 9 Hz, 1H, ArH), 6.72 (d, J=9 Hz, 1H, ArH), 5.62-5.95 (brs, 2H, NH$_2$), 3.92 (s, 3H, CH$_3$).

Example 2

Methyl 2-amino-3-iodo-5-(trifluoromethyl)benzoate, Compound 2

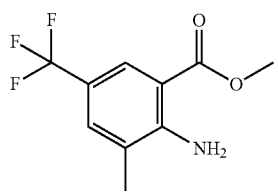

A solution of methyl 2-amino-5-(trifluoromethyl)benzoate (0.59 g, 2.7 mmoles) in trifluoroacetic acid (5 ml) was treated with N-iodosuccinimide (0.68 g, 3.0 mmoles) and stirred at ambient temperature for 18 h. The mixture was evaporated to dryness and the residue treated with water (25 ml) and basified with potassium carbonate then extracted with dichloromethane (25 ml). The organic phase was then washed with 10% sodium metabisulphite solution (25 ml), separated and dried over sodium sulphate, filtered and evaporated to dryness. The residue was chromatographed on silica gel eluting with an ethyl acetate/isohexane gradient. This gave the title compound 2 as a white solid (0.633 g, 68%).

$^1$H-NMR (CDCl$_3$, 300 MHz) δ 8.18 (d, J=3 Hz, 1H, ArH), 8.01 (d, J=3 Hz, 1H, ArH), 6.55-7.05 (brs, 2H, NH$_2$), 3.92 (s, 3H, CH$_3$).

Example 3

Methyl 2-amino-3-methyl-5-(trifluoromethyl)benzoate, Compound 3

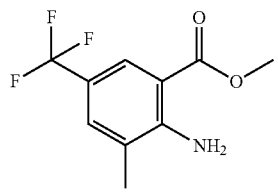

A mixture of methyl 2-amino-3-iodo-5-(trifluoromethyl)benzoate (0.633 g, 1.83 mmoles), trimethylboroxine (0.56 ml, 3.66 mmoles), cesium carbonate (1.2 g, 3.66 mmoles) and 1,1'-bis(diphenylphosphino)ferrocene-palladium(II) dichloride dichloromethane complex (0.075 g, 0.09 mmoles) in 1,4-dioxane (15 mL) was heated in a microwave reactor at 130° C. for 1.5 h. The mixture was partitioned between water (30 ml) and ethyl acetate (2×30 ml). The combined organics were dried over sodium sulphate, filtered and evaporated to dryness. The residue was chromatographed on silica gel eluting with an ethyl acetate/isohexane gradient. This gave the title compound 3 as an orange solid (0.41 g, 96%).

$^1$H-NMR (CDCl$_3$, 300 MHz) δ 8.07 (s, 1H, ArH), 7.38 (s, 1H, ArH), 6.05-7.35 (brs, 2H, NH$_2$), 3.92 (s, 3H, CH$_3$).

Scheme 1. Synthesis of Compounds 4 and 8

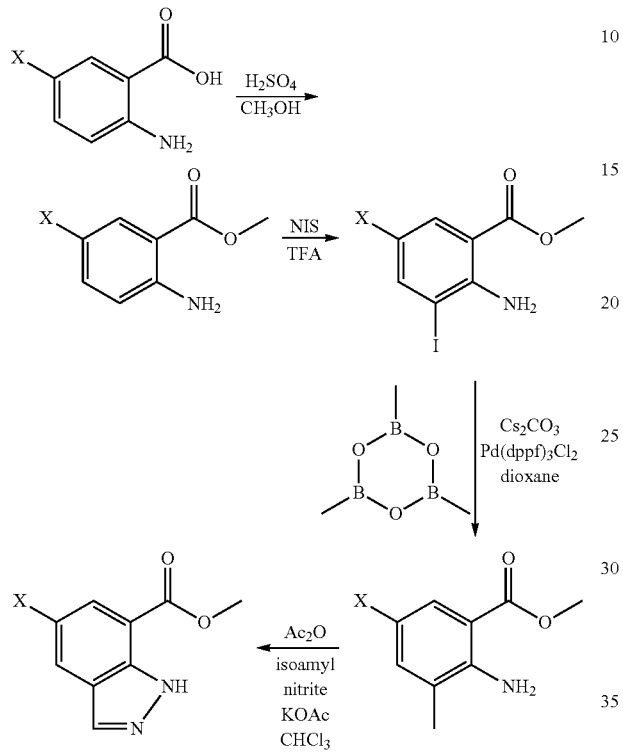

Example 4

Methyl 5-(trifluoromethyl)-1H-indazole-7-carboxylate, Compound 4

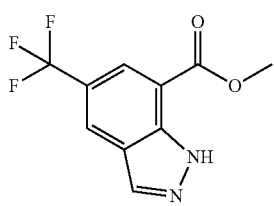 [SMILES: COC(=O)c1cc(C(F)(F)F)cc2cn[nH]c12]

To a solution of compound 3, at 0° C. and under nitrogen atmosphere, in chloroform (0.3M) was added acetic anhydride (2.3 equiv.) drop wise and the resulting mixture was stirred for 1 h at r.t. Then potassium acetate (0.2 equiv.) was added followed by addition of isoamyl nitrite (2.2 equiv.) and the resulting mixture was heated at reflux for 16 h. After, the reaction was cooled down to r.t. While cooling, a solid precipitation was observed. The solid was filtrated and dried under vacuum to give the title compound 4. (0.324 g, 75%).

$^1$H-NMR (CDCl$_3$, 300 MHz) δ 11.40-11.60 (brs, 1H, ArH), 8.31 (s, 2H, 2× ArH), 8.28 (d, J=2 Hz. 1H, ArH), 4.07 (s, 3H, CH$_3$).

Example 5

Methyl 2-amino-5-(trifluoromethoxy)benzoate, Compound 5

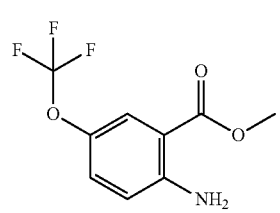

The title compound was prepared as in the method of compound 1 from 2-amino-5-(trifluoromethoxy)benzoic acid to give a pale yellow oil (0.538 g, 46%).

$^1$H-NMR (CDCl$_3$, 300 MHz) δ 7.73 (d, J=3 Hz, 1H, ArH), 7.18 (dd, J=3 and 9 Hz, 1H, ArH), 6.66 (d, J=9 Hz, 1H, ArH), 5.67-5.91 (brs, 2H, NH$_2$), 3.89 (s, 3H, CH$_3$).

Example 6

Methyl 2-amino-3-iodo-5-(trifluoromethoxy)benzoate, Compound 6

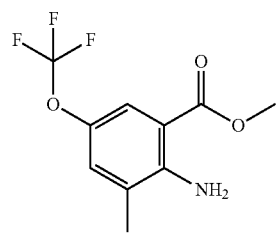 [SMILES: COC(=O)c1cc(OC(F)(F)F)cc(C)c1N]

The title compound was prepared as in the method of compound 2 from methyl 2-amino-5-(trifluoromethoxy)benzoate to give a white solid (0.67 g, 82%).

$^1$H-NMR (CDCl$_3$, 300 MHz) δ 7.81 (d, J=3 Hz, 1H, ArH), 7.71 (d, J=3 Hz. 1H, ArH), 5.35-5.55 (brs, 2H, NH$_2$), 3.92 (s, 3H, CH$_3$).

Example 7

Methyl 2-amino-3-methyl-5-(trifluoromethoxy)benzoate, Compound 7

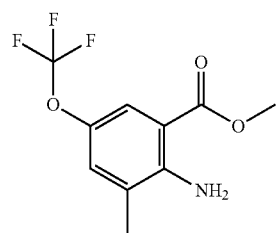 [SMILES: COC(=O)c1cc(OC(F)(F)F)cc(C)c1N]

The title compound was prepared as in the method of compound 3 from methyl 2-amino-3-iodo-5-(trifluoromethoxy)benzoate to give an orange oil (0.413 g, 89%).

¹H-NMR (CDCl₃, 300 MHz) δ 7.65 (d, J=3 Hz, 1H, ArH), 7.11 (d, J=3 Hz, 1H, ArH), 5.74-6.02 (brs, 2H, NH₂), 3.89 (s, 3H, CH₃), 2.19 (s, 3H, CH₃).

Example 8

Methyl 5-(trifluoromethoxy)-1H-indazole-7-carboxylate, Compound 8

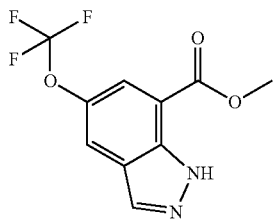 [SMILES: COC(=O)c1cc(OC(F)(F)F)cc2cn[nH]c12]

The title compound was prepared as in the method of compound 4 from methyl 2-amino-3-methyl-5-(trifluoromethoxy)benzoate to give an off-white solid (0.355 g, 83%).

¹H-NMR (CDCl₃, 300 MHz) δ 11.39 (s, 1H, NH), 8.19 (s, 1H, ArH), 7.97 (s, 1H, ArH), 7.86 (s, 1H, ArH), 4.06 (s, 3H, CH₃).

General Method 1: Alkylation

To a solution of 5-substituted-indazole-7-carboxylic acid methyl ester, at room temperature and under nitrogen atmosphere, in N,N-dimethylformamide (0.18M) were added Cesium carbonate (1.2 equiv.) and the corresponding alkylating agent (1.1 equiv.). The resulting mixture was stirred for 18 h. Then, the reaction mixture was concentrated to dryness under vacuum and the residue was partitioned between ethyl acetate (20 mL) and water (20 mL). The organic layer was separated, washed with Brine, dried (MgSO₄), filtered and the solvent evaporated.

The mixture of regioisomers was separated by column chromatography in a SPE Silica cartridge using as eluent a gradient from iso-hexane/ethyl acetate 9:1 to 1:3 to isolate both regioisoisomers as colorless oils.

Example 9

5-Chloro-1-isobutyl-1H-indazole-7-carboxylic acid methyl ester, Compound 9

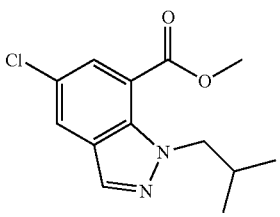 [SMILES: COC(=O)c1cc(Cl)cc2cnn(CC(C)C)c12]

Compound 9 was prepared following general method 1, using 5-chloro-1H-indazole-7-carboxylic acid methyl ester (see WO2011008572 which is incorporated by reference in its entirety) as starting material and 1-iodo-2-methylpropane as alkylating agent. Yield: 48%.

¹H-NMR (CDCl₃, 300 MHz) δ 8.01 (s, 1H, ArH), 7.86 (s, 2H, ArH), 4.55 (d, 2H, J=7.3 Hz, NCH₂), 3.99 (s, 3H, OCH₃), 2.02 (m, 1H, —CH(CH₃)₂), 0.80 (d, 6H, J=6.7 Hz, CH(CH₃)₂.

LC-MS: m/z 267 M+H⁺

Example 10

5-Bromo-1-isobutyl-1H-indazole-7-carboxylic acid methyl ester, Compound 10

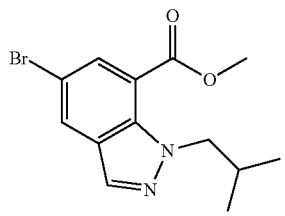

Compound 10 was prepared following general method 1, using 5-bromo-1H-indazole-7-carboxylic acid methyl ester as starting material and 1-iodo-2-methylpropane as alkylating agent. Yield: 70%.

¹H-NMR (CDCl₃, 300 MHz) δ 8.05 (s, 1H, ArH), 8.00 (s, 1H, ArH), 7.95 (s, 1H, ArH), 4.55 (d, 2H, J=7.3 Hz, NCH₂), 3.99 (s, 3H, OCH₃), 2.02 (m, 1H, —CH(CH₃)₂), 0.80 (d, 6H, J=6.7 Hz, CH(CH₃)₂.

LC-MS: m/z 312 M+H⁺

Example 11

5-Fluoro-1-isobutyl-1H-indazole-7-carboxylic acid methyl ester, Compound 11

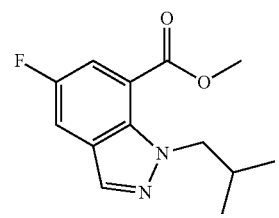 [SMILES: COC(=O)c1cc(F)cc2cnn(CC(C)C)c12]

Compound 11 was prepared following general method 1, using 5-fluoro-1H-indazole-7-carboxylic acid methyl ester (see WO2011008572, incorporated by reference in its entirety) as starting material and 1-iodo-2-methylpropane as alkylating agent. Yield: 41%.

¹H-NMR (CDCl₃, 300 MHz) δ 8.04 (s, 1H, ArH), 7.70 (dd, J=3 and 10 Hz, 1H, ArH), 7.57 (dd, J=3 and 10 Hz, 1H, ArH), 4.58 (d, J=7 Hz, 2H, CH₂), 4.01 (s, 3H, CH₃), 1.97-2.09 (m, 1H, CH), 0.79 (d, J=8 Hz, 6H, 2×CH₃).

Example 12

1-Isobutyl-5-trifluoromethyl-1H-indazole-7-carboxylic acid methyl ester, Compound 12

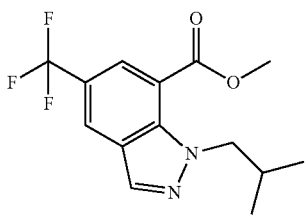 [SMILES: COC(=O)c1cc(C(F)(F)F)cc2cnn(CC(C)C)c12]

Compound 12 was prepared following general method 1, using compound 4 as starting material and 1-iodo-2-methylpropane as alkylating agent. Yield: 39%.

$^1$H-NMR (CDCl$_3$, 300 MHz) δ 8.22 (s, 1H, ArH), 8.19 (s, 1H, ArH), 8.15 (s, 1H, ArH), 4.62 (d, J=5 Hz, 2H, CH$_2$), 4.03 (s, 3H, CH$_3$), 1.99-2.14 (m, 1H, CH), 0.82 (d, J=8 Hz, 6H, 2×CH$_3$).

Example 13

1-Isobutyl-5-trifluoromethoxy-1H-indazole-7-carboxylic acid methyl ester, Compound 13

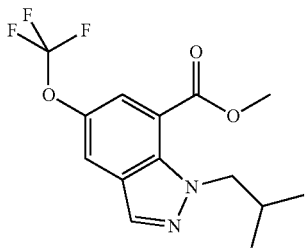 [SMILES: COC(=O)c1cc(OC(F)(F)F)cc2cnn(CC(C)C)c12]

Compound 13 was prepared following general method 1, using compound 8 as starting material and 1-iodo-2-methylpropane as alkylating agent. Yield: 56%.

$^1$H-NMR (CDCl$_3$, 300 MHz) δ 11.39 (s, 1H, NH), 8.19 (s, 1H, ArH), 7.97 (s, 1H, ArH), 7.86 (s, 1H, ArH), 4.06 (s, 3H, CH$_3$).

Example 14

5-bromo-1-isopropyl-1H-indazole-7-carboxylic acid methyl ester, Compound 14

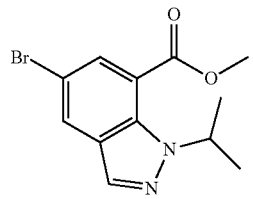 [SMILES: COC(=O)c1cc(Br)cc2cnn(C(C)C)c12]

Compound 14 was prepared following general method 1, using 5-bromo-1H-indazole-7-carboxylic acid methyl ester as a starting material and 2-iodopropane as alkylating agent. Yield: 65%.

$^1$H-NMR (CDCl$_3$, 300 MHz) δ 8.05 (s, 1H, ArH), 8.00 (d, 1H, J=2 Hz, ArH), 7.93 (d, 1H, J=2 Hz, ArH), 5.30 (m, 1H, —CH(CH$_3$)$_2$), 4.00 (s, 3H, OCH$_3$), 1.55 (d, 6H, J=6.7 Hz, CH(CH$_3$)$_2$).

LC-MS: m/z 298 M+H$^+$

Example 15

5-Bromo-1-(2-ethyl-butyl)-1H-indazole-7-carboxylic acid methyl ester, Compound 15

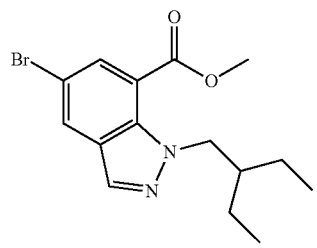 [SMILES: CCC(CC)Cn1ncc2cc(Br)cc(C(=O)OC)c21]

Compound 15 was prepared following general method 1, using 5-bromo-1H-indazole-7-carboxylic acid methyl ester as a starting material and 3-chloromethyl-pentane as alkylating agent. Yield: 22%.

$^1$H-NMR (CDCl$_3$, 300 MHz) δ 8.10 (s, 1H, ArH), 8.03 (s, 1H, ArH), 7.93 (s, 1H, ArH), 4.38 (d, 2H, J=7.3 Hz, NCH$_2$), 3.99 (s, 3H, OCH$_3$), 2.10 (m, 1H, —CH(CH$_2$CH$_3$)$_2$), 1.30 (m, 4H, —CH(CH$_2$CH$_3$)$_2$), 0.90 (m, 6H, —CH(CH$_2$CH$_3$)$_2$).

LC-MS: m/z 340 M+H$^+$

Example 16

5-Chloro-1-Propyl-1H-indazole-7-carboxylic acid methyl ester, Compound 16

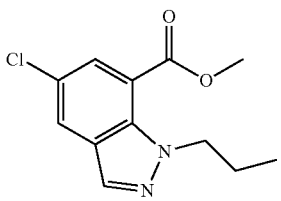 [SMILES: CCCn1ncc2cc(Cl)cc(C(=O)OC)c21]

Compound 16 was prepared following general method 1, using 5-chloro-1H-indazole-7-carboxylic acid methyl ester (WO2011008572) as a starting material and 1-iodopropane as alkylating agent. Yield: 39%.

$^1$H-NMR (CDCl$_3$, 300 MHz) δ 8.02 (s, 1H, ArH), 7.87 (dd, 2H, J=2, 6.2 Hz, ArH), 4.66 (t, 2H, J=7.3 Hz, NCH$_2$), 4.00 (s, 3H, OCH$_3$), 1.78 (m, 2H, —CH$_2$CH$_2$CH$_3$), 0.86 (m, 3H, —CH$_2$CH$_2$CH$_3$).

LC-MS: m/z 253 M+H$^+$

General Method 2: Ester Reduction

To a solution of ester derivative (9 to 16), at room temperature and under nitrogen atmosphere, in dry toluene (5M) were added a 2M solution of DIBAH in toluene (5 equiv.). The resulting mixture was stirred for 18 h. Then, the reaction mixture was quenched with 10% Rochelle's salt solution and the mixture was extracted with ethyl acetate. The organic layer was separated, washed with brine, dried (MgSO₄), filtered and the solvent evaporated to give the desired product as a colorless solid.

Example 17

(5-Chloro-1-isobutyl-1H-indazole-7-yl)-methanol, Compound 17

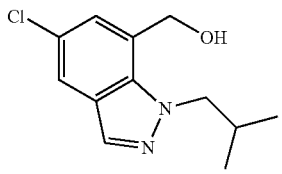 [SMILES: CC(C)Cn1ncc2cc(Cl)cc(CO)c21]

Compound 17 was prepared following general method 2, using compound 9 as a starting material. Yield: 91%.
$^1$H-NMR (CDCl$_3$, 500 MHz) δ 7.95 (s, 1H, ArH), 7.66 (s, 1H, ArH), 7.29 (s, 1H, ArH), 4.98 (s, 2H, —CH$_2$OH), 4.41 (d, 2H, J=7.3 Hz, NCH), 2.23 (m, 1H, —CH(CH$_3$)$_2$), 2.01 (s, 1H, OH), 0.90 (d, 6H, J=6.7 Hz, CH(CH$_3$)$_2$.
LC-MS: m/z 239 M+H$^+$

Example 18

(5-Bromo-1-isobutyl-1H-indazole-7-yl)-methanol, Compound 18

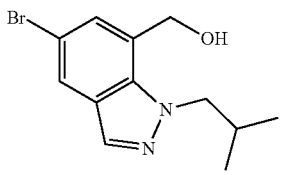 [SMILES: CC(C)Cn1ncc2cc(Br)cc(CO)c21]

Compound 18 was prepared following general method 2, using compound 10 as a starting material. Yield: 90%.
$^1$H-NMR (CDCl$_3$, 300 MHz) δ 7.95 (s, 1H, ArH), 7.83 (s, 1H, ArH), 7.40 (s, 1H, ArH), 5.00 (s, 2H, —CH$_2$OH), 4.42 (d, 2H, J=7.3 Hz, NCH$_2$), 2.28 (m, 1H, —CH(CH$_3$)$_2$), 0.95 (d, 6H, J=6.7 Hz, CH(CH$_3$)$_2$.
LC-MS: m/z 284 M+H$^+$

Example 19

(5-Fluoro-1-isobutyl-1H-indazole-7-yl)-methanol, Compound 19

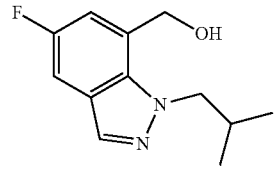 [SMILES: CC(C)Cn1ncc2cc(F)cc(CO)c21]

Compound 19 was prepared following general method 2, using compound 11 as a starting material. Yield: 93%.

$^1$H-NMR (CDCl$_3$, 300 MHz) δ 7.94 (s, 1H, ArH), 7.29 (dd, J=3 and 10 Hz, 1H, ArH), 7.17 (dd, J=3 and 10 Hz, 1H, ArH), 4.98 (s, 2H, CH$_2$), 4.38 (d, J=7 Hz, 2H, CH$_2$), 2.38-2.53 (brs, 1H, OH), 2.14-2.28 (m, 1H, CH), 0.92 (d, J=8 Hz, 6H, 2×CH$_3$).

Example 20

(1-Isobutyl-5-trifluoromethane-1H-indazole-7-yl)-methanol, Compound 20

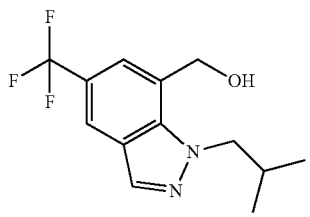 [SMILES: CC(C)Cn1ncc2cc(C(F)(F)F)cc(CO)c21]

Compound 20 was prepared following general method 2, using compound 12 as a starting material. Yield: 93%.
$^1$H-NMR (CDCl$_3$, 300 MHz) δ 8.08 (s, 1H, ArH), 8.01 (s, 1H, ArH), 7.55 (s, 1H, ArH), 5.07 (s, 2H, CH$_2$), 4.47 (d, J=5 Hz, 2H, CH$_2$), 2.19-2.34 (m, 1H, CH), 0.97 (d, J=8 Hz, 6H, 2×CH$_3$).

Example 21

(1-Isobutyl-5-trifluoromethoxy-1H-indazole-7-yl)-methanol, Compound 21

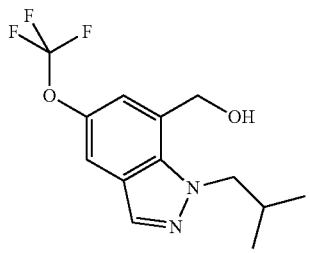 [SMILES: CC(C)Cn1ncc2cc(OC(F)(F)F)cc(CO)c21]

Compound 21 was prepared following general method 2, using compound 13 as a starting material. Yield: 100%.
$^1$H-NMR (CDCl$_3$, 300 MHz) δ 8.01 (s, 1H, ArH), 7.54 (s, 1H, ArH), 7.24 (s, 1H, ArH), 5.01 (d, J=6 Hz, 2H, CH$_2$), 4.44 (d, J=7.5 Hz, 2H, CH$_2$), 2.18-2.32 (m, 1H, CH), 2.09 (t, J=6 Hz, 1H, OH), 0.95 (d, J=8 Hz, 6H, 2×CH$_3$).

Example 22

(5-Bromo-1-isopropyl-1H-indazol-7-yl)-methanol, Example 22

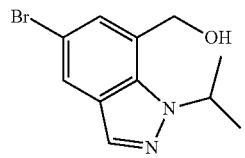

Compound 22 was prepared following general method 2, using compound 14 as a starting material. Yield: 92%.

$^{1}$H-NMR (CDCl$_3$, 300 MHz) δ 8.02 (s, 1H, ArH), 7.83 (s, 1H, ArH), 7.40 (s, 1H, ArH), 5.25 (m, 1H, —NCH(CH$_3$)$_2$), 5.00 (s, 2H, —CH$_2$OH), 1.60 (d, 6H, J=6.7 Hz, CH(CH$_3$)$_2$.

LC-MS: m/z 270 M+H$^+$

Example 23

[5-Bromo-1-(2-ethyl-butyl)-1H-indazol-7-yl]methanol, Compound 23

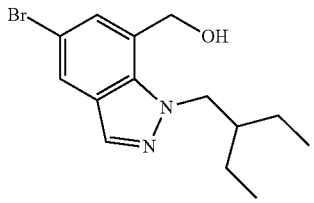 [SMILES: CCC(CC)Cn1ncc2cc(Br)cc(CO)c21]

Compound 23 was prepared following general method 2, using compound 15 as a starting material. Yield: 90%.

$^{1}$H-NMR (CDCl$_3$, 300 MHz) δ 7.83 (s, 1H, ArH), 7.70 (s, 1H, ArH), 7.30 (s, 1H, ArH), 5.05 (s, 2H, CH$_2$OH), 4.25 (d, 2H, J=7.3 Hz, NCH$_2$), 2.00 (m, 1H, —CH(CH$_2$CH$_3$)$_2$), 1.25 (m, 4H, —CH(CH$_2$CH$_3$)$_2$), 0.90 (m, 6H, —CH(CH$_2$CH$_3$)$_2$).

LC-MS: m/z 312 M+H$^+$

Example 24

(5-Chloro-1-propyl-1H-indazol-7-yl)-methanol, Compound 24

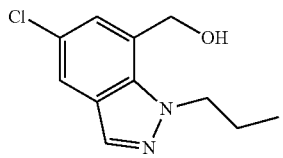

Compound 24 was prepared following general method 2, using compound 16 as a starting material. Yield: 89%.

$^{1}$H-NMR (CDCl$_3$, 300 MHz) δ 7.90 (s, 1H, ArH), 7.62 (m, 2H, ArH), 7.26 (m, 1H, ArH), 4.95 (s, 2H, CH$_2$OH), 4.55 (t, 2H, J=7.3 Hz, NCH$_2$), 1.88 (m, 2H, —CH$_2$CH$_2$CH$_3$), 0.94 (m, 3H, —CH$_2$CH$_2$CH$_3$).

LC-MS: m/z 225 M+H$^+$

General Method 3A: Preparation of Methylsulfonate Derivative and Reaction with Corresponding Heterocycles To a solution of benzyl alcohol derivative, at room temperature and under nitrogen atmosphere, in dry dichloromethane (6M) were added DIPEA (1.1 equivalents) methane sulfonic anhydride. (1.1 equivalents) The resulting mixture was stirred for 2 h. Then, the reaction mixture was quenched with water and the mixture was extracted with more dichloromethane. The organic layer was separated, washed with Brine, dried (MgSO$_4$), filtered and the solvent evaporated to give the desired product as yellow oil.

To a solution of heterocycle, at room temperature and under nitrogen atmosphere, in dry DMF (4M) was added a solution of the methylsulfonate (1.1 equiv) prepared above in dry DMF followed by caesium carbonate (1.2 equivalents). The resulting mixture was stirred for 16 h at room temperature. Then, the reaction mixture was diluted with ethyl acetate and 2M solution of HCl. The organic layer was separated, washed with Brine, dried (MgSO4), filtered and the solvent evaporated. The residue was purified in a 20G SPE cartridge using a eluent gradient from isohexane/ethyl acetate 9:1 to 1:1 as appropriate to isolate the desired product.

General Method 3B. Preparation of Methylsulfonate Derivative and Reaction with Corresponding Heterocycles To a solution of benzyl alcohol derivative, at room temperature and under nitrogen atmosphere, in dry dichloromethane (6M) were added DIPEA (1.1 equivalents) methane sulfonic anhydride. (1.1 equivalents) The resulting mixture was stirred for 2 h. Then, the reaction mixture was quenched with water and the mixture was extracted with more dichloromethane. The organic layer was separated, washed with Brine, dried (MgSO$_4$), filtered and the solvent evaporated to give the desired product as yellow oil.

To a solution of heterocycle, at room temperature and under nitrogen atmosphere, in dry DMF (4M) was added sodium hydride 60% (1.3 equivalents) and the resulting mixture was stirred for 30 min. A solution of the methylsulfonate (1.1 equiv) prepared above in dry DMF was then added and the resulting mixture was stirred for 16 h at room temperature. Then, the reaction mixture was diluted with ethyl acetate and water. The organic layer was separated, washed with Brine, dried (MgSO$_4$), filtered and the solvent evaporated. The residue was purified in a 20G SPE cartridge using a eluent gradient from isohexane/ethyl acetate 9:1 to 1:1 as appropriate to isolate the desired product.

Example 25

1-(5-Chloro-1-isobutyl-1H-indazol-7-ylmethyl)-1H-indazole-5-carboxylic acid methyl ester, Compound 25

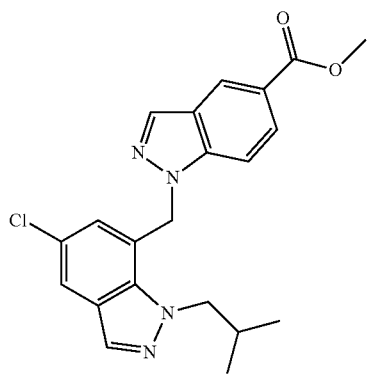

Compound 25 was prepared following general method 3A, using compound 17 as a starting material and 1H-indazole-5-carboxylic acid methyl ester as the heterocycle. Yield: 40%.

$^{1}$H-NMR (CDCl$_3$, 300 MHz) δ 8.60 (s, 1H, ArH), 8.25 (s, 1H, ArH), 8.05 (d, 1H, J=8.9 Hz, ArH), 8.00 (s, 1H, ArH), 7.63 (s, 1H, ArH), 7.30 (d, 1H, J=8.9 Hz, ArH), 6.75 (s, 1H, ArH), 6.00 (s, 2H, ArCH$_2$N), 4.42 (d, 2H, J=7.3 Hz, NCH$_2$), 3.95 (s, 3H, —CO$_2$CH$_3$), 2.25 (m, 1H, —CH(CH$_3$)$_2$), 0.90 (d, 6H, J=6.7 Hz, CH(CH$_3$)$_2$.

LC-MS: m/z 397 M+H$^+$

Example 26

1-(5-Bromo-1-isobutyl-1H-indazol-7-ylmethyl)-1H-indazole-5-carboxylic acid methyl ester, Compound 26

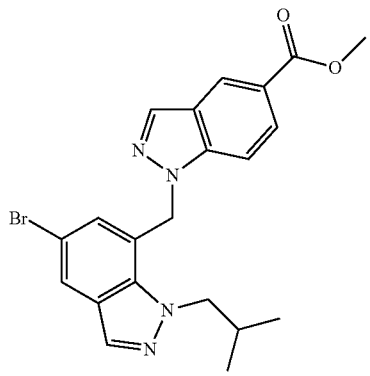 [SMILES: COC(=O)c1ccc2c(cnn2Cc2cc(Cl)cc3cnn(CC(C)C)c23)c1]

Compound 26 was prepared following general method 3A, using compound 18 as a starting material and 1H-indazole-5-carboxylic acid methyl ester as the heterocycle. Yield: 65%.

$^1$H-NMR (CDCl$_3$, 300 MHz) δ 8.55 (s, 1H, ArH), 8.20 (s, 1H, ArH), 8.10 (d, 1H, J=8.9 Hz, ArH), 7.85 (s, 1H, ArH), 7.30 (d, 1H, J=8.9 Hz, ArH), 7.27 (s, 1H, ArH), 6.90 (s, 1H, ArH), 6.00 (s, 2H, ArCH$_2$N), 4.40 (d, 2H, J=7.3 Hz, NCH$_2$), 3.95 (s, 3H, —CO$_2$CH$_3$), 2.30 (m, 1H, —CH(CH$_3$)$_2$), 0.85 (d, 6H, J=6.7 Hz, CH(CH$_3$)$_2$.

LC-MS: m/z 442 M+H$^+$

Example 27

1-(5-Fluoro-1-isobutyl-1H-indazol-7-ylmethyl)-1H-indazole-5-carboxylic acid methyl ester, Compound 27

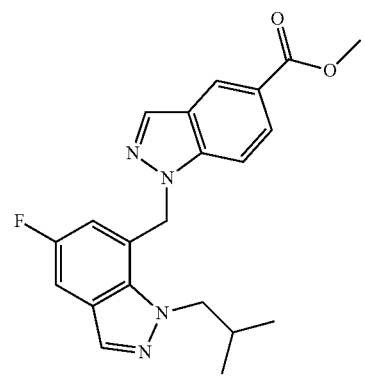 [SMILES: COC(=O)c1ccc2c(cnn2Cc2cc(F)cc3cnn(CC(C)C)c23)c1]

Compound 27 was prepared following general method 3A, using compound 19 as a starting material and 1H-indazole-5-carboxylic acid methyl ester as the heterocycle. Yield: 53%.

$^1$H-NMR (CDCl$_3$, 300 MHz) δ 8.58 (s, 1H, ArH), 8.25 (s, 1H, ArH), 8.07 (dd, J=2 and 7.5 Hz. 1H, ArH), 8.01 (s, 1H, ArH), 7.27-7.33 (m, 2H, 2× ArH), 6.46 (dd, J=4 and 10.5 Hz, 1H, ArH), 6.05 (s, 2H, CH$_2$), 4.38 (d, J=5 Hz, 2H, CH$_2$), 3.95 (s, 3H, CH$_3$), 2.25-2.38 (m, 1H, CH), 0.95 (d, J=8 Hz, 6H, 2×CH$_3$).

Example 28

1-(1-Isobutyl-5-trifluoromethyl-1H-indazol-7-ylmethyl)-1H-indazole-5-carboxylic acid methyl ester, Compound 28

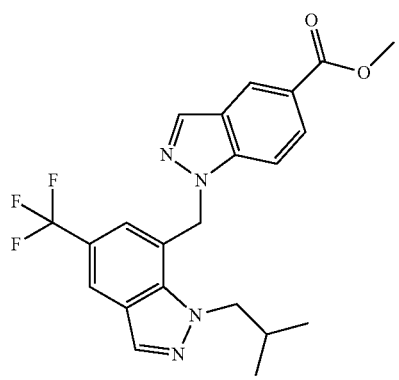 [SMILES: COC(=O)c1ccc2c(cnn2Cc2cc(C(F)(F)F)cc3cnn(CC(C)C)c23)c1]

Compound 28 was prepared following general method 3A, using compound 20 as a starting material and 1H-indazole-5-carboxylic acid methyl ester as the heterocycle. Yield: 41%.

$^1$H-NMR (CDCl$_3$, 300 MHz) δ 8.58 (s, 1H, ArH), 8.21 (s, 1H, ArH), 8.17 (s, 1H, ArH), 8.01-8.09 (m, 2H, 2×ArH), 7.29 (s, 1H, ArH), 7.09 (s, 1H, ArH), 6.05 (s, 2H, CH$_2$), 4.41 (d, J=5 Hz, 2H, CH$_2$), 3.98 (s, 3H, CH$_3$), 2.23-2.38 (m, 1H, CH), 0.93 (d, J=8 Hz, 6H, 2×CH$_3$).

Example 29

1-(1-Isobutyl-5-trifluoromethoxy-1H-indazol-7-ylmethyl)-1H-indazole-5-carboxylic acid methyl ester, Compound 29

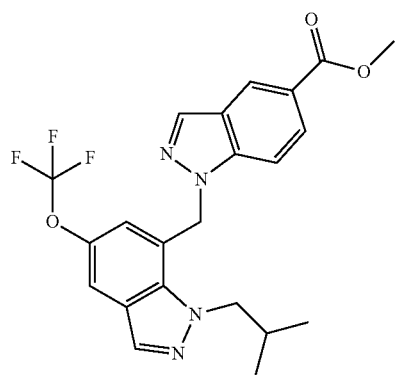 [SMILES: COC(=O)c1ccc2c(cnn2Cc2cc(OC(F)(F)F)cc3cnn(CC(C)C)c23)c1]

Compound 29 was prepared following general method 3A, using compound 21 as a starting material and 1H-indazole-5-carboxylic acid methyl ester as the heterocycle. Yield: 46%.

$^1$H-NMR (CDCl$_3$, 300 MHz) δ 8.58 (s, 1H, ArH), 8.22 (s, 1H, ArH), 8.02-8.08 (m, 2H, 2×ArH), 7.54 (s, 1H, ArH), 7.29 (d, J=5 Hz, 1H, ArH), 6.61 (s, 1H, ArH), 6.01 (s, 2H, CH$_2$), 4.41 (d, J=7.5 Hz, 2H, CH₂), 3.95 (s, 3H, CH₃), 2.25-2.39 (m, 1H, CH), 0.95 (d, J=8 Hz, 6H, 2×CH₃).

Example 30

1-(5-Bromo-1-isopropyl-1H-indazol-7-ylmethyl)-1H-indazole-5-carboxylic acid methyl ester, Compound 30

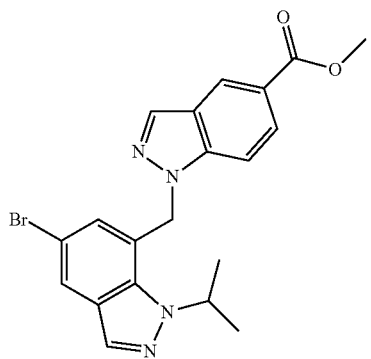 [SMILES: COC(=O)c1ccc2c(cnn2Cc2cc(Br)cc3cnn(C(C)C)c23)c1]

Compound 30 was prepared following general method 3A, using compound 22 as a starting material and 1H-indazole-5-carboxylic acid methyl ester as the heterocycle. Yield: 30%.

$^1$H-NMR (CDCl₃, 300 MHz) δ 8.53 (s, 1H, ArH), 8.20 (s, 1H, ArH), 8.03 (d, 1H, J=8.9 Hz, ArH), 7.95 (s, 1H, ArH), 7.70 (s, 1H, ArH), 7.25 (d, 1H, J=8.9 Hz, ArH), 7.03 (s, 1H, ArH), 5.95 (s, 2H, ArCH₂N), 5.60 (m, 1H, NCH(CH₃)₂), 3.95 (s, 3H, —CO₂CH₃), 1.45 (d, 6H, J=6.7 Hz, NCH(CH₃)₂.
LC-MS: m/z 428 M+H⁺

Example 31

1-[5-Bromo-1-(2-ethyl-butyl)-1H-indazol-7-ylmethyl]-1H-indazole-5-carboxylic acid methyl ester, Compound 31

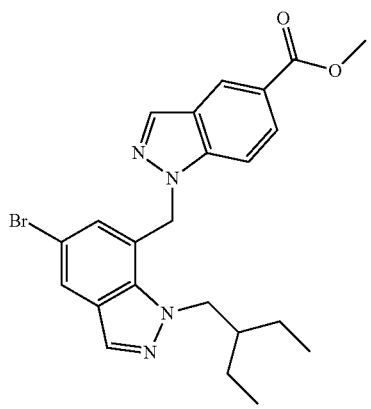 [SMILES: CCC(CC)Cn1ncc2cc(Br)cc(Cn3ncc4cc(C(=O)OC)ccc43)c21]

Compound 31 was prepared following general method 3A, using compound 23 as a starting material and 1H-indazole-5-carboxylic acid methyl ester as the heterocycle. Yield: 47%.

$^1$H-NMR (CDCl₃, 300 MHz) δ 8.51 (s, 1H, ArH), 8.17 (s, 1H, ArH), 8.05 (d, 1H, J=8.9 Hz, ArH), 7.82 (s, 1H, ArH), 7.73 (s, 1H, ArH), 7.65 (d, 1H, J=8.9 Hz, ArH), 6.95 (s, 1H, ArH), 6.00 (s, 2H, ArCH₂N), 4.30 (d, 2H, J=7.3 Hz, NCH₂), 3.95 (s, 3H, —CO₂CH₃), 2.03 (m, 1H, —CH(CH₂CH₃)₂), 1.30 (m, 4H, CH(CH₂CH₃)₂, 0.90 (m, 6H, CH(CH₂CH₃)₂.
LC-MS: m/z 470 M+H⁺

Example 32

1-[5-Chloro-1-(2-propyl)-1H-indazol-7-ylmethyl]-1H-indazole-5-carboxylic acid methyl ester, Compound 32

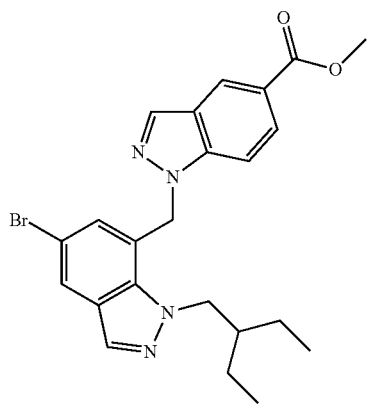 [SMILES: CCC(CC)Cn1ncc2cc(Br)cc(Cn3ncc4cc(C(=O)OC)ccc43)c21]

Compound 32 was prepared following general method 3A, using compound 24 as a starting material and 1H-indazole-5-carboxylic acid methyl ester as the heterocycle. Yield: 47%.

$^1$H-NMR (CDCl₃, 300 MHz) δ 8.57 (s, 1H, ArH), 8.20 (s, 1H, ArH), 8.05 (d, 1H, J=8.9 Hz, ArH), 7.94 (s, 1H, ArH), 7.64 (s, 1H, ArH), 7.30 (d, 1H, J=8.9 Hz, ArH), 6.80 (s, 1H, ArH), 6.00 (s, 2H, ArCH₂N), 4.55 (t, 2H, J=7.3 Hz, NCH₂CH₂CH₃), 3.96 (s, 3H, —CO₂CH₃), 1.89 (m, 2H, NCH₂CH₂CH₃), 0.97 (t, 3H, J=7.3 Hz, NCH₂CH₂CH₃).
LC-MS: m/z 383 M+H⁺

Example 33

1-(5-Chloro-1-isobutyl-1H-indazol-7-ylmethyl)-1H-pyrazolo[3,4-b]pyridine-5-carboxylic acid methyl ester, Compound 33

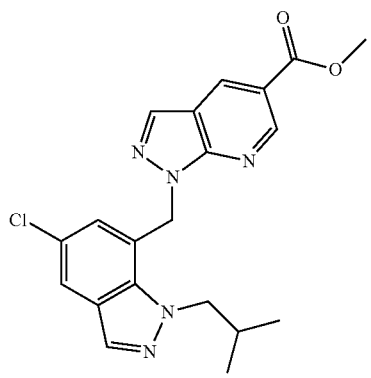 [SMILES: COC(=O)c1cnc2c(cnn2Cc2cc(Cl)cc3cnn(CC(C)C)c23)c1]

Compound 33 was prepared following general method 3A, using compound 17 as a starting material and 1H-pyrazolo[3,4-b]pyridine-5-carboxylic acid methyl ester as the heterocycle. Yield: 53%.

¹H-NMR (CDCl₃, 300 MHz) δ 9.25 (s, 1H, ArH), 8.80 (s, 1H, ArH), 8.20 (s, 1H, ArH), 8.00 (s, 1H, ArH), 7.67 (s, 1H, ArH), 7.10 (s, 1H, ArH), 6.10 (s, 2H, ArCH₂N), 4.55 (d, 2H, J=7.3 Hz, NCH₂), 3.97 (s, 3H, —CO₂CH₃), 2.37 (m, 1H, —CH(CH₃)₂), 0.95 (d, 6H, J=6.7 Hz, CH(CH₃)₂.
LC-MS: m/z 398 M+H⁺

Example 34

1-(5-Chloro-1-isobutyl-1H-indazol-7-ylmethyl)-1H-benzoimidazole-5-carboxylic acid methyl ester, Compound 34

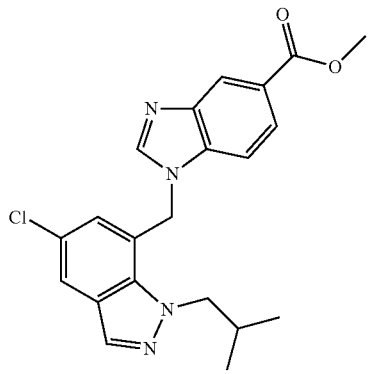 [SMILES: COC(=O)c1ccc2c(c1)ncn2Cc1cc(Cl)cc2cnn(CC(C)C)c12]

Compound 34 was prepared following general method 3A, using compound 17 as a starting material and 1H-benzoimidazole-5-carboxylic acid methyl ester as the heterocycle. Yield: 40%.

¹H-NMR (CDCl₃, 300 MHz) δ 8.62 (s, 1H, ArH), 8.09 (d 1H, J=8.5 Hz, ArH), 8.03 (s, 1H, ArH), 7.75 (s, 1H, ArH), 7.40 (d, 1H, J=8.5 Hz, ArH), 7.29 (s, 1H, ArH), 6.92 (s, 1H, ArH), 5.73 (s, 2H, ArCH₂N), 4.09 (d, 2H, J=7.3 Hz, NCH₂), 3.98 (s, 3H, —CO₂CH₃), 2.12 (m, 1H, —CH(CH₃)₂), 0.82 (d, 6H, J=6.7 Hz, CH(CH₃)₂.
LC-MS: m/z 397 M+H⁺

Example 35

3-(5-Chloro-1-isobutyl-1H-indazol-7-ylmethyl)-3H-imidazo[4,5-b]pyridine-6-carboxylic acid methyl ester, Compound 35

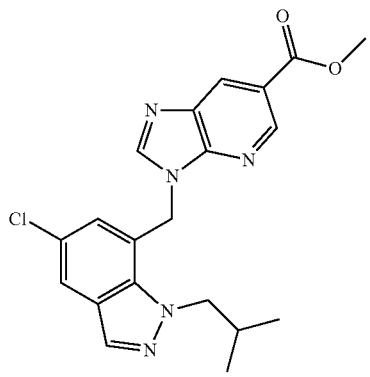 [SMILES: COC(=O)c1cnc2c(c1)ncn2Cc1cc(Cl)cc2cnn(CC(C)C)c12]

Compound 35 was prepared following general method 3A, using compound 17 as a starting material and 3H-Imidazo[4,5-b]pyridine-6-carboxylic acid methyl ester as the heterocycle. Yield: 30%.

¹H-NMR (CDCl₃, 300 MHz) δ 9.17 (s, 1H, ArH), 8.76 (s 1H, ArH), 8.00 (s, 1H, ArH), 7.92 (s, 1H, ArH), 7.76 (s, 1H, ArH), 7.16 (s, 1H, ArH), 5.85 (s, 2H, ArCH₂N), 4.08 (d, 2H, J=7.3 Hz, NCH₂), 4.01 (s, 3H, —CO₂CH₃), 2.20 (m, 1H, —CH(CH₃)₂), 0.87 (d, 3H, J=6.7 Hz, CH(CH₃)₂, 0.78 (d, 3H, J=6.7 Hz, CH(CH₃)₂ LC-MS: m/z 398 M+H⁺

Example 36

1-(5-Chloro-1-isobutyl-1H-indazol-7-ylmethyl)-1H-pyrrolo[2,3-b]pyridine-5-carboxylic acid methyl ester, Compound 36

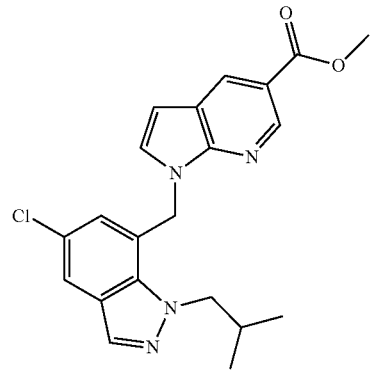 [SMILES: COC(=O)c1cnc2c(ccn2Cc2cc(Cl)cc3cnn(CC(C)C)c23)c1]

Compound 36 was prepared following general method 3A, using compound 17 as a starting material and 1H-Pyrrolo[2,3-b]pyridine-5-carboxylic acid methyl ester as the heterocycle. Yield: 73%.

¹H-NMR (CDCl₃, 300 MHz) δ 9.07 (d, J=2 Hz, 1H, ArH), 8.65 (d, J=2 Hz, 1H, ArH), 7.98 (s, 1H, ArH), 7.71 (d, J=2 Hz, 1H, ArH), 7.05-7.08 (m, 2H, 2× ArH), 6.58 (d, J=3 Hz, 1H, ArH), 5.85 (s, 2H, CH₂), 4.07 (d, J=7.5 Hz, 2H, CH₂), 3.98 (s, 3H, CH₃), 2.12-2.28 (m, 1H, CH), 0.75 (d, J=8 Hz, 6H, 2×CH₃).

Example 37

1-(5-Bromo-1-isobutyl-1H-indazol-7-ylmethyl)-3-methyl-1H-indazole-5-carboxylic acid methyl ester, Compound 37

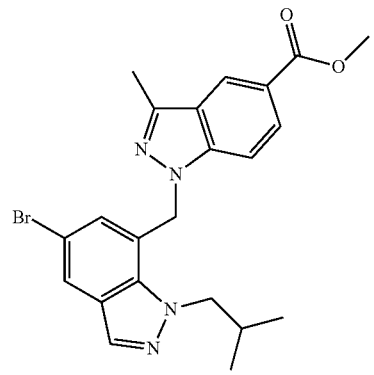

Compound 37 was prepared following general method 3A, using compound 18 as a starting material and 3-methyl-1H-indazole-5-carboxylic acid methyl ester as the heterocycle. Yield: 76%.

¹H-NMR (CDCl₃, 300 MHz) δ 8.50 (s, 1H, ArH), 8.03 (d, 1H, J=8.9 Hz, ArH), 7.95 (s, 1H, ArH), 7.68 (s, 1H, ArH), 7.15 (d, 1H, J=8.9 Hz, ArH), 6.85 (s, 1H, ArH), 5.92 (s, 2H, ArCH₂N), 4.35 (d, 2H, J=7.3 Hz, NCH₂), 3.93 (s, 3H, —CO₂CH₃), 2.65 (s, 3H, CH₃), 2.25 (m, 1H, —CH(CH₃)₂), 0.85 (d, 6H, J=6.7 Hz, CH(CH₃)₂.

LC-MS: m/z 457 M+H⁺

Example 38

1-(5-Bromo-1-isobutyl-1H-indazol-7-ylmethyl)-3-methyl-1H-pyrazolo[3,4-b]pyridine-5-carboxylic acid methyl ester, Compound 38

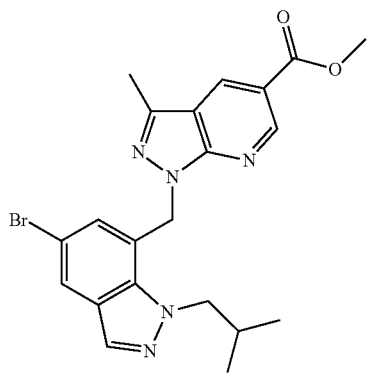

Compound 38 was prepared following general method 3A, using compound 18 as a starting material and 3-Methyl-1H-pyrazolo[3,4-b]pyridine-5-carboxylic acid methyl ester as the heterocycle. Yield: 50%.

¹H-NMR (CDCl₃, 300 MHz) δ 9.20 (s, 1H, ArH), 8.70 (s, 1H, ArH), 7.95 (s, 1H, ArH), 7.78 (s, 1H, ArH), 7.15 (s, 1H, ArH), 6.05 (s, 2H, ArCH₂N), 4.53 (d, 2H, J=7.3 Hz, NCH₂), 4.00 (s, 3H, —CO₂CH₃), 2.62 (s, 3H, CH₃), 2.32 (m, 1H, —CH(CH₃)₂), 0.95 (d, 3H, J=6.7 Hz, CH(CH₃)₂, 0.85 (d, 3H, J=6.7 Hz, CH(CH₃)₂.

LC-MS: m/z 458 M+H⁺

Example 39

1-(1-Isobutyl-5-trifluoromethyl-1H-indazol-7-ylmethyl)-1H-benzoimidazole-5-carboxylic acid methyl ester, Compound 39

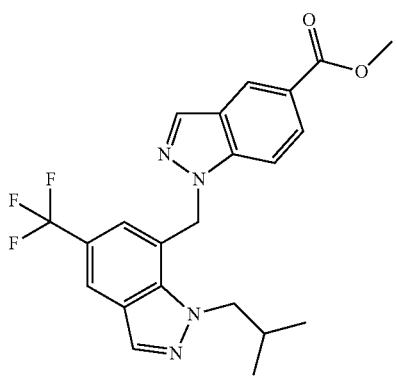 [SMILES: COC(=O)c1ccc2c(cnn2Cc2cc(C(F)(F)F)cc3cnn(CC(C)C)c23)c1]

Compound 39 was prepared following general method 3A, using compound 20 as a starting material and 1H-benzoimidazole-5-carboxylic acid methyl ester as the heterocycle.

¹H-NMR (CDCl₃, 300 MHz) δ 8.74 (s, 1H, ArH), 8.13-8.23 (m, 3H, 3×ArH), 7.83 (s, 1H, ArH), 7.47 (d, J=9 Hz, 1H, ArH), 7.27 (s, 1H, ArH), 5.80 (s, 2H, CH₂), 4.08 (d, J=5 Hz, 2H, CH₂), 2.15-2.31 (m, 1H, CH), 0.81 (d, J=8 Hz, 6H, 2×CH₃).

LC-MS: m/z 417 (M+H⁺).

Example 40

1-(1-Isobutyl-5-trifluoromethoxy-1H-indazol-7-ylmethyl)-1H-benzoimidazole-5-carboxylic acid methyl ester, Compound 40

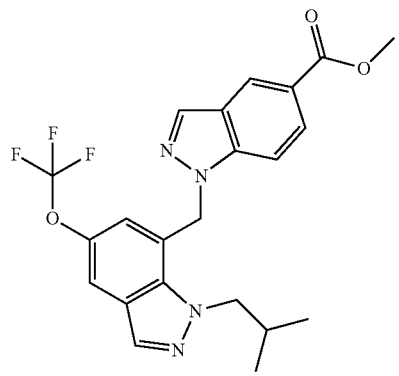

Compound 40 was prepared following general method 3A, using compound 21 as a starting material and 1H-benzoimidazole-5-carboxylic acid methyl ester as the heterocycle. Yield: 65%.

¹H-NMR (CDCl₃, 300 MHz) δ 8.63 (s, 1H, ArH), 8.11 (s, 1H, ArH), 8.09 (s, 1H, ArH), 7.83 (s, 1H, ArH), 7.65 (s, 1H, ArH), 7.38 (d, J=9 Hz, 1H, ArH), 6.80 (s, 1H, ArH), 5.77 (s, 2H, CH₂), 4.14 (d, J=7.5 Hz, 2H, CH₂), 3.97 (s, 3H, CH₃), 2.18-2.32 (m, 1H, CH), 0.88 (d, J=8 Hz, 6H, 2×CH₃).

General Method 4: Ester Hydrolysis

To a solution of methyl ester derivative (25 to 40) in dioxane (6M) was added a 2M aqueous solution of sodium hydroxide. (4 equivalents) The resulting mixture was heated at 60° C. for 16 h. Then, the reaction mixture was allowed to cool, neutralised to pH 7 with 2M solution of HCl and diluted with ethyl acetate. The organic layer was separated, washed with Brine, dried (MgSO₄), filtered and the solvent evaporated to give the desired product as yellow oil. The residue was purified in a 20G SPE cartridge using an eluent gradient from isohexane/ethyl acetate 9:1 to 1:1 as appropriate to isolate the desired product.

Scheme 2. Synthesis of compounds 41-56

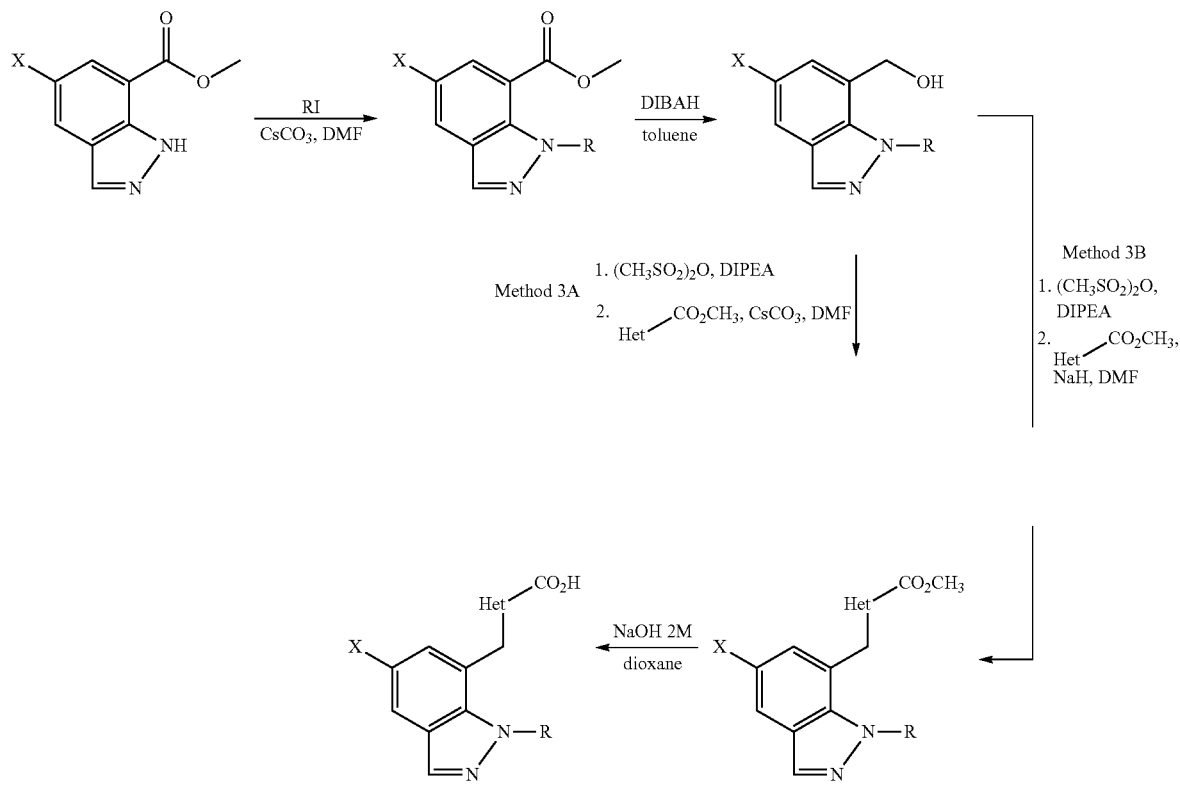

Example 41

1-(5-Chloro-1-isobutyl-1H-indazol-7-ylmethyl)-1H-indazole-5-carboxylic acid, Compound 41

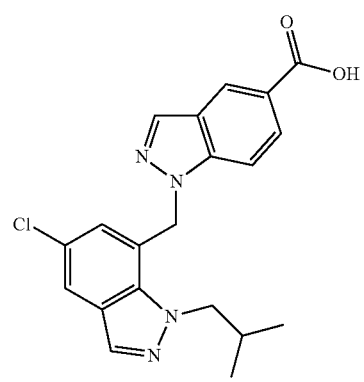 [SMILES: CC(C)Cn1ncc2cc(Cl)cc(Cn3ncc4cc(C(=O)O)ccc43)c21]

Example 42

1-(5-Bromo-1-isobutyl-1H-indazol-7-ylmethyl)-1H-indazole-5-carboxylic acid, Compound 42

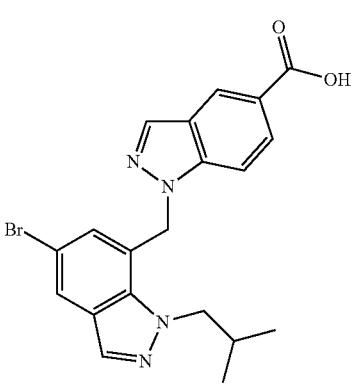

Compound 41 was prepared from compound 25 following general method 4. Yield: 80%.

$^1$H-NMR (CDCl$_3$, 300 MHz) δ 8.65 (s, 1H, ArH), 8.25 (s, 1H, ArH), 8.10 (d, 1H, J=8.9 Hz, ArH), 8.00 (s, 1H, ArH), 7.65 (s, 1H, ArH), 7.33 (d, 1H, J=8.9 Hz, ArH), 6.75 (s, 1H, ArH), 6.03 (s, 2H, ArCH$_2$N), 4.35 (d, 2H, J=7.3 Hz, NCH$_2$), 1.55 (m, 1H, —CH(CH$_3$)$_2$), 0.85 (d, 6H, J=6.7 Hz, CH(CH$_3$)$_2$.

LC-MS: m/z 383 M+H$^+$

Compound 42 was prepared from compound 26 following general method 4. Yield: 80%.

$^1$H-NMR (CDCl$_3$, 300 MHz) δ 8.67 (s, 1H, ArH), 8.25 (s, 1H, ArH), 8.10 (d, 1H, J=8.9 Hz, ArH), 8.00 (s, 1H, ArH), 7.83 (s, 1H, ArH), 7.35 (d, 1H, J=8.9 Hz, ArH), 6.97 (s, 1H, ArH), 6.03 (s, 2H, ArCH$_2$N), 4.37 (d, 2H, J=7.3 Hz, NCH$_2$), 2.25 (m, 1H, —CH(CH$_3$)$_2$), 0.95 (d, 3H, J=6.7 Hz, CH(CH$_3$)$_2$, 0.85 (d, 3H, J=6.7 Hz, CH(CH$_3$)$_2$.

LC-MS: m/z 429 M+H$^+$

Example 43

1-(5-Fluoro-1-isobutyl-1H-indazol-7-ylmethyl)-1H-indazole-5-carboxylic acid, Compound 43

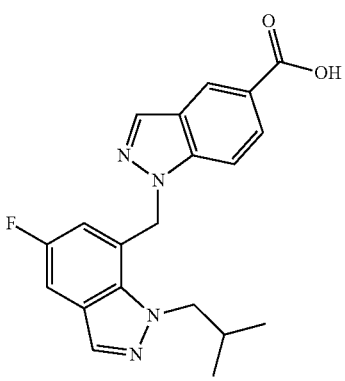 [SMILES: CC(C)Cn1ncc2cc(F)cc(Cn3ncc4cc(C(=O)O)ccc43)c21]

Compound 43 was prepared from compound 27 following general method 4. Yield: 54%.

$^1$H-NMR (CDCl$_3$, 300 MHz) δ 8.69 (s, 1H, ArH), 8.28 (s, 1H, ArH), 8.13 (dd, J=2 and 7.5 Hz. 1H, ArH), 8.01 (s, 1H, ArH), 7.27-7.38 (m, 2H, 2×ArH), 6.48 (dd, J=4 and 10.5 Hz, 1H, ArH), 6.05 (s, 2H, CH$_2$), 4.43 (d, J=5 Hz, 2H, CH$_2$), 2.25-2.38 (m, 1H, CH), 0.95 (d, J=8 Hz, 6H, 2×CH$_3$).

LC-MS: m/z 367 (M+H$^+$).

Example 44

1-(1-Isobutyl-5-trifluoromethyl-1H-indazol-7-ylmethyl)-1H-indazole-5-carboxylic acid, Compound 44

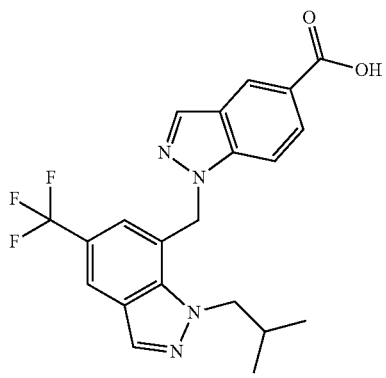 [SMILES: CC(C)Cn1ncc2cc(C(F)(F)F)cc(Cn3ncc4cc(C(=O)O)ccc43)c21]

Compound 44 was prepared from compound 28 following general method 4. Yield: 54%.

$^1$H-NMR (CDCl$_3$, 300 MHz) δ 8.68 (s, 1H, ArH), 8.27 (s, 1H, ArH), 8.17 (s, 1H, ArH), 8.11 (dd, J=2 and 9 Hz, 1H, ArH), 8.05 (s, 1H, ArH), 7.33 (d, J=9 Hz, 1H, ArH), 7.13 (s, 1H, ArH), 6.05 (s, 2H, CH$_2$), 4.41 (d, J=5 Hz, 2H, CH$_2$), 2.23-2.38 (m, 1H, CH), 0.93 (d, J=8 Hz, 6H, 2×CH$_3$).

LC-MS: m/z 417 (M+H$^+$).

Example 45

1-(1-Isobutyl-5-trifluoromethoxy-1H-indazol-7-ylmethyl)-1H-indazole-5-carboxylic acid, Compound 45

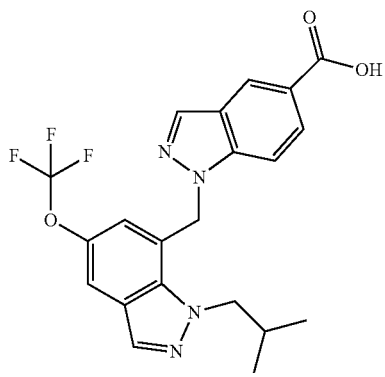 [SMILES: CC(C)Cn1ncc2cc(OC(F)(F)F)cc(Cn3ncc4cc(C(=O)O)ccc43)c21]

Compound 45 was prepared from compound 29 following general method 4. Yield: 62%.

$^1$H-NMR (CDCl$_3$, 300 MHz) δ 8.69 (s, 1H, ArH), 8.27 (s, 1H, ArH), 8.04-8.14 (m, 2H, 2×ArH), 7.54 (s, 1H, ArH), 7.32 (d, J=5 Hz, 1H, ArH), 6.63 (s, 1H, ArH), 6.03 (s, 2H, CH$_2$), 4.42 (d, J=7.5 Hz, 2H, CH$_2$), 2.24-2.40 (m, 1H, CH), 0.95 (d, J=8 Hz, 6H, 2×CH$_3$).

LC-MS: m/z 433 (M+H$^+$).

Example 46

1-(5-Bromo-1-isopropyl-1H-indazol-7-ylmethyl)-1H-indazole-5-carboxylic acid, Compound 46

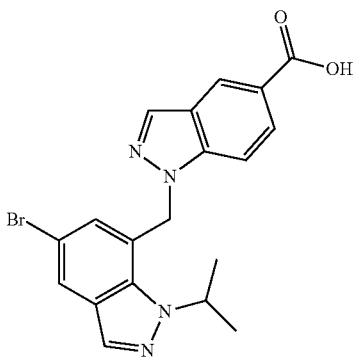 [SMILES: CC(C)n1ncc2cc(Br)cc(Cn3ncc4cc(C(=O)O)ccc43)c21]

Compound 46 was prepared from compound 30 following general method 4. Yield: 85%.

$^1$H-NMR (CDCl$_3$, 300 MHz) δ 8.55 (s, 1H, ArH), 8.20 (s, 1H, ArH), 8.00 (d, 1H, J=8.9 Hz, ArH), 7.97 (s, 1H, ArH), 7.80 (s, 1H, ArH), 7.23 (d, 1H, J=8.9 Hz, ArH), 6.97 (s, 1H, ArH), 5.95 (s, 2H, ArCH$_2$N), 5.05 (m, 1H, NCH(CH$_3$)$_2$), 1.40 (d, 6H, J=6.7 Hz, NCH(CH$_3$)$_2$.

LC-MS: m/z 415 M+H$^+$

Example 47

1-[5-Bromo-1-(2-ethyl-butyl)-1H-indazol-7-ylmethyl]-1H-indazole-5-carboxylic acid, Compound 47

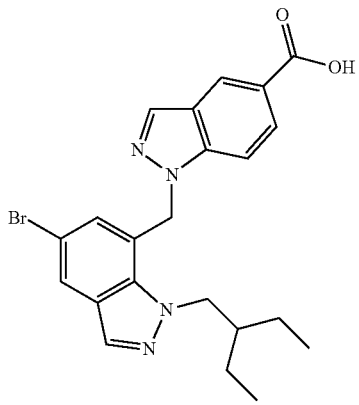 [SMILES: CCC(CC)Cn1ncc2cc(Br)cc(Cn3ncc4cc(C(=O)O)ccc43)c21]

Compound 47 was prepared from compound 31 following general method 4. Yield: 90%.

$^1$H-NMR (CDCl$_3$, 300 MHz) δ 8.63 (s, 1H, ArH), 8.20 (s, 1H, ArH), 8.05 (d, 1H, J=8.9 Hz, ArH), 7.80 (s, 1H, ArH), 7.70 (s, 1H, ArH), 7.65 (d, 1H, J=8.9 Hz, ArH), 7.00 (s, 1H, ArH), 6.00 (s, 2H, ArCH$_2$N), 4.30 (d, 2H, J=7.3 Hz, NCH$_2$), 2.00 (m, 1H, —CH(CH$_2$CH$_3$)$_2$), 1.30 (m, 4H, CH(CH$_2$CH$_3$)$_2$), 0.90 (m, 6H, CH(CH$_2$CH$_3$)$_2$.

LC-MS: m/z 457 M+H$^+$

Example 48

1-[5-Chloro-1-(2-propyl)-1H-indazol-7-ylmethyl]-1H-indazole-5-carboxylic acid, Compound 48

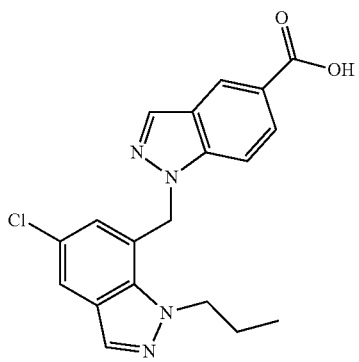 [SMILES: CCCn1ncc2cc(Cl)cc(Cn3ncc4cc(C(=O)O)ccc43)c21]

Compound 48 was prepared from compound 32 following general method 4. Yield: 65%.

$^1$H-NMR (CDCl$_3$, 300 MHz) δ 8.67 (s, 1H, ArH), 8.25 (s, 1H, ArH), 8.11 (d, 1H, J=8.9 Hz, ArH), 7.99 (s, 1H, ArH), 7.68 (s, 1H, ArH), 7.35 (d, 1H, J=8.9 Hz, ArH), 6.81 (s, 1H, ArH), 6.02 (s, 2H, ArCH$_2$N), 4.55 (t, 2H, J=7.3 Hz, NCH$_2$CH$_2$CH$_3$), 1.86 (m, 2H, NCH$_2$CH$_2$CH$_3$), 0.88 (t, 3H, J=7.3 Hz, NCH$_2$CH$_2$CH$_3$).

LC-MS: m/z 369 M+H$^+$

Example 49

1-(5-Chloro-1-isobutyl-1H-indazol-7-ylmethyl)-1H-pyrazolo[3,4-b]pyridine-5-carboxylic acid, Compound 49

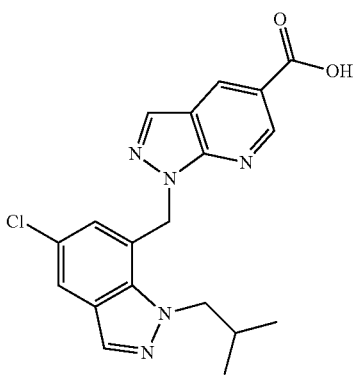 [SMILES: CC(C)Cn1ncc2cc(Cl)cc(Cn3ncc4cc(C(=O)O)cnc43)c21]

Compound 49 was prepared from compound 33 following general method 4. Yield: 60%.

$^1$H-NMR (CDCl$_3$, 300 MHz) δ 9.23 (s, 1H, ArH), 8.76 (s, 1H, ArH), 8.06 (s, 1H, ArH), 7.93 (s, 1H, ArH), 7.60 (s, 1H, ArH), 7.01 (s, 1H, ArH), 6.02 (s, 2H, ArCH$_2$N), 4.47 (d, 2H, J=7.3 Hz, NCH$_2$), 2.26 (m, 1H, —CH(CH$_3$)$_2$), 0.88 (d, 6H, J=6.7 Hz, CH(CH$_3$)$_2$.

LC-MS: m/z 384 M+H$^+$

Example 50

1-(5-Chloro-1-isobutyl-1H-indazol-7-ylmethyl)-1H-benzoimidazole-5-carboxylic acid, Compound 50

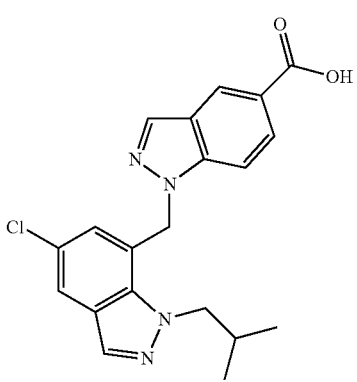 [SMILES: CC(C)Cn1ncc2cc(Cl)cc(Cn3ncc4cc(C(=O)O)ccc43)c21]

Compound 50 was prepared from compound 34 following general method 4. Yield: 70%.

$^1$H-NMR (CH$_3$OD, 300 MHz) δ 8.52 (s, 1H, ArH), 8.33 (bs 1H, ArH), 8.12 (s, 1H, ArH), 8.09 (s, 1H, ArH), 7.81 (s, 1H, ArH), 7.60 (d, 1H, J=8.5 Hz, ArH), 6.85 (s, 1H, ArH), 6.02 (s, 2H, ArCH$_2$N), 4.21 (d, 2H, J=7.3 Hz, NCH$_2$), 2.23 (m, 1H, —CH(CH$_3$)$_2$), 0.80 (d, 6H, J=6.7 Hz, CH(CH$_3$)$_2$.

LC-MS: m/z 383 M+H$^+$

Example 51

3-(5-Chloro-1-isobutyl-1H-indazol-7-ylmethyl)-3H-imidazo[4,5-b]pyridine-6-carboxylic acid, Compound 51

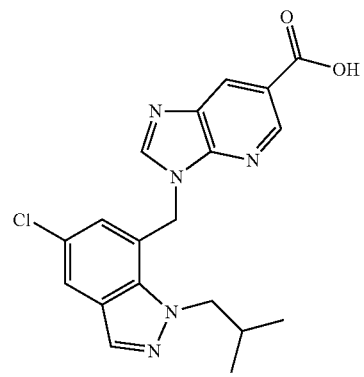 [SMILES: CC(C)Cn1ncc2cc(Cl)cc(Cn3cnc4cc(C(=O)O)cnc43)c21]

Compound 51 was prepared from compound 35 following general method 4. Yield: 70%.

$^1$H-NMR (CDCl$_3$, 300 MHz) δ 9.31 (s, 1H, ArH), 8.90 (s 1H, ArH), 8.14 (s, 1H, ArH), 8.11 (s, 1H, ArH), 7.91 (s, 1H, ArH), 7.47 (s, 1H, ArH), 6.01 (s, 2H, ArCH$_2$N), 4.25 (d, 2H, J=7.3 Hz, NCH$_2$), 2.33 (m, 1H, —CH(CH$_3$)$_2$), 0.91 (d, 6H, J=6.7 Hz, CH(CH$_3$)$_2$.

LC-MS: m/z 384 M+H$^+$

Example 52

1-(5-Chloro-1-isobutyl-1H-indazol-7-ylmethyl)-1H-pyrrolo[2,3-b]pyridine-5-carboxylic acid, Compound 52

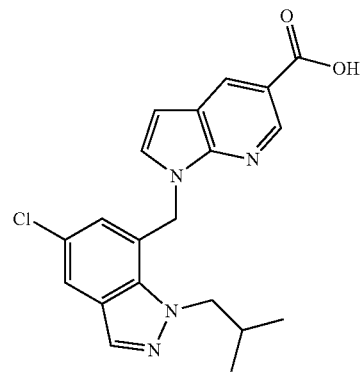 [SMILES: CC(C)Cn1ncc2cc(Cl)cc(Cn3ccc4cc(C(=O)O)cnc43)c21]

Compound 52 was prepared from compound 36 following general method 4. Yield: 66%.

$^1$H-NMR (CDCl$_3$, 300 MHz) δ 9.02 (d, J=2 Hz, 1H, ArH), 8.62 (d, J=2 Hz, 1H, ArH), 7.95 (s, 1H, ArH), 7.70 (d, J=2 Hz, 1H, ArH), 7.03 (d, J=3 Hz, 1H, ArH), 6.99 (d, J=2 Hz, 1H, ArH), 6.57 (d, J=3 Hz, 1H, ArH), 5.85 (s, 2H, CH$_2$), 4.05 (d, J=7.5 Hz, 2H, CH$_2$), 2.07-2.23 (m, 1H, CH), 0.71 (d, J=8 Hz, 6H, 2×CH$_3$).

LC-MS: m/z 383 and 385 (M+H$^+$).

Example 53

1-(5-Bromo-1-isobutyl-1H-indazol-7-ylmethyl)-3-methyl-1H-indazole-5-carboxylic acid, Compound 53

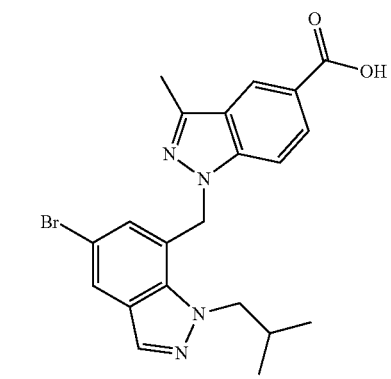

Compound 53 was prepared from compound 37 following general method 4. Yield: 50%.

$^1$H-NMR (CDCl$_3$, 300 MHz) δ 8.60 (s, 1H, ArH), 8.10 (d, 1H, J=8.9 Hz, ArH), 7.97 (s, 1H, ArH), 7.80 (s, 1H, ArH), 7.20 (d, 1H, J=8.9 Hz, ArH), 6.90 (s, 1H, ArH), 5.92 (s, 2H, ArCH$_2$N), 4.40 (d, 2H, J=7.3 Hz, NCH$_2$), 2.70 (s, 3H, CH$_3$), 2.20 (m, 1H, —CH(CH$_3$)$_2$), 0.85 (d, 6H, J=6.7 Hz, CH(CH$_3$)$_2$.

LC-MS: m/z 443 M+H$^+$

Example 54

1-(5-Bromo-1-isobutyl-1H-indazol-7-ylmethyl)-3-methyl-1H-pyrazolo[3,4-b]pyridine-5-carboxylic HCl salt, Compound 54

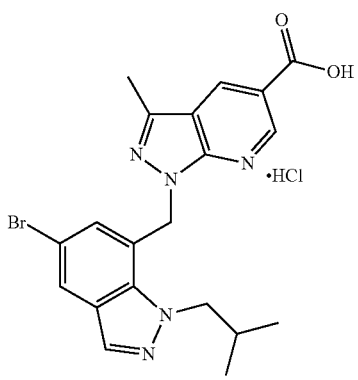 [SMILES: Cc1nn(Cc2cc(Br)cc3cnn(CC(C)C)c23)c2ncc(C(=O)O)cc12 ; Cl]

Compound 54 was prepared from compound 38 following general method 4. Yield: 60%.

$^1$H-NMR (CH$_3$OD, 300 MHz) δ 9.20 (s, 1H, ArH), 8.85 (s, 1H, ArH), 8.05 (s, 1H, ArH), 7.90 (s, 1H, ArH), 7.20 (s, 1H, ArH), 6.10 (s, 2H, ArCH$_2$N), 4.55 (d, 2H, J=7.3 Hz, NCH$_2$), 2.65 (s, 3H, CH$_3$), 2.32 (m, 1H, —CH(CH$_3$)$_2$), 0.90 (d, 6H, J=6.7 Hz, CH(CH$_3$)$_2$.

LC-MS: m/z 444 M+H$^+$

Example 55

1-(1-Isobutyl-5-trifluoromethyl-1H-indazol-7-ylmethyl)-1H-benzoimidazole-5-carboxylic acid, Compound 55

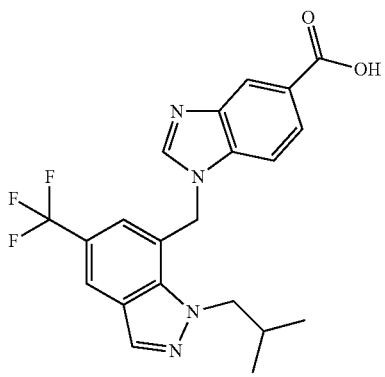 [SMILES: CC(C)Cn1ncc2cc(C(F)(F)F)cc(Cn3cnc4cc(C(=O)O)ccc43)c21]

Compound 55 was prepared from compound 39 following general method 4. Yield: 13%.

$^1$H-NMR (CDCl$_3$, 300 MHz) δ 8.74 (s, 1H, ArH), 8.13-8.23 (m, 3H, 3×ArH), 7.83 (s, 1H, ArH), 7.47 (d, J=9 Hz, 1H, ArH), 7.27 (s, 1H, ArH), 5.80 (s, 2H, CH$_2$), 4.08 (d, J=5 Hz, 2H, CH$_2$), 2.15-2.31 (m, 1H, CH), 0.81 (d, J=8 Hz, 6H, 2×CH$_3$).

LC-MS: m/z 417 (M+H$^+$).

Example 56

1-(1-Isobutyl-5-trifluoromethoxy-1H-indazol-7-ylmethyl)-1H-benzoimidazole-5-carboxylic acid, Compound 56

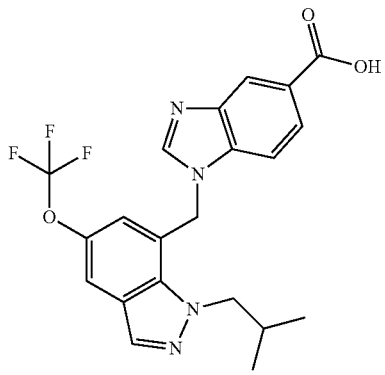 [SMILES: CC(C)Cn1ncc2cc(OC(F)(F)F)cc(Cn3cnc4cc(C(=O)O)ccc43)c21]

Compound 56 was prepared from compound 40 following general method 4. Yield: 65%.

$^1$H-NMR (CD$_3$OD, 300 MHz) δ 8.55 (s, 1H, ArH), 8.02-8.11 (m, 2H, 2×ArH), 7.95 (s, 1H, ArH), 7.32-7.41 (m, 2H, 2×ArH), 6.71 (s, 1H, ArH), 5.82 (s, 2H, CH$_2$), 4.11 (d, J=7.5 Hz, 2H, CH$_2$), 2.11-2.29 (m, 1H, CH), 0.82 (d, J=8 Hz, 6H, 2×CH$_3$).

LC-MS: m/z 433 (M+H$^+$).

Example 57

2-(5-Chloro-1-isobutyl-indazol-7-yl)acetonitrile, Compound 57

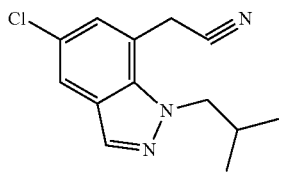 [SMILES: CC(C)Cn1ncc2cc(Cl)cc(CC#N)c21]

To a solution of compound 17 (1 g, 4.2 mmol), at room temperature and under nitrogen atmosphere, in dry dichloromethane (10 mL) were added DIPEA (0.8 mL, 4.62 mmol) and methane sulfonic anhydride. (0.8 g, 4.62 mmol) The resulting mixture was stirred for 2 h. Then, the reaction mixture was quenched with water and the mixture was extracted with more dichloromethane. The organic layer was separated, washed with Brine, dried (MgSO$_4$), filtered and the solvent evaporated to give the desired product as yellow oil.

The residue (4.2 mmol) was dissolved in DMF (20 ml), treated with sodium cyanide (0.4 g, 8.2 mmol) and stirred at 80° C. under a nitrogen atmosphere for 1 h. The mixture was evaporated to dryness and the residue partitioned between water (50 ml) and ethyl acetate (2×50 ml). The combined organics were washed with saturated brine (50 ml) then dried over sodium sulphate, filtered and evaporated to dryness. This gave the title compound as a brown oil (0.994 g, 82%).

$^1$H-NMR (CDCl$_3$, 300 MHz) δ 7.97 (s, 1H, ArH), 7.71 (s, 1H, ArH), 7.41 (s, 1H, ArH), 4.32 (d, J=7.5 Hz, 2H, CH$_2$), 4.12 (s, 2H, CH$_2$), 2.15-2.30 (m, 1H, CH), 0.96 (d, J=8 Hz, 6H, 2×CH$_3$).

Example 58

2-(5-Chloro-1-isobutyl-indazol-7-yl)acetic acid, Compound 58

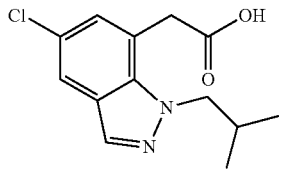 [SMILES: CC(C)Cn1ncc2cc(Cl)cc(CC(=O)O)c21]

A solution of compound 57 (0.16 g, 0.65 mmoles) in conc hydrochloric acid (1 ml) was heated at 50° C. for 1 h. Water (1 ml) was added and the mixture heated at 80° C. for 18 h. The mixture was cooled and water (10 ml) added then extracted with ethyl acetate (2×15 ml). The combined organics were dried over sodium sulphate, filtered and evaporated to dryness to give the title compound as an off-white solid (0.155 g, 90%).

$^1$H-NMR (CDCl$_3$, 300 MHz) δ 9.20-10.20 (brs, 1H, OH), 7.97 (s, 1H, ArH), 7.66 (d, J=2 Hz, 1H, ArH), 7.22 (d, J=2 Hz, 1H, ArH), 4.31 (d, J=7.5 Hz, 2H, CH$_2$), 3.99 (s, 2H, CH$_2$), 2.09-2.23 (m, 1H, CH), 0.91 (d, J=8 Hz, 6H, 2×CH$_3$).

Example 59

Methyl 2-[[[2-(5-chloro-1-isobutyl-indazol-7-yl) acetyl]amino]methyl]pyridine-4-carboxylate, Compound 59

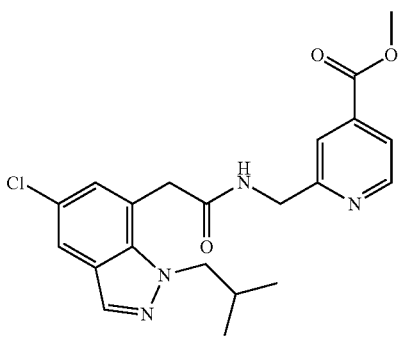 [SMILES: COC(=O)c1ccnc(CNC(=O)Cc2cc(Cl)cc3cnn(CC(C)C)c23)c1]

A mixture of compound 58 (0.155 g, 0.58 mmoles) and methyl 2-(aminomethyl)pyridine-4-carboxylate dihydrochloride (0.139 g, 0.58 mmoles) (see WO2003070732, example 6, step 2 for preparation, which is incorporated by reference in its entirety) in dichloromethane (20 ml) was treated with N,N,N',N'-tetramethyl-O-(1H-benzotriazol-1-yl)uranium hexafluorophosphate (0.264 g, 0.69 mmoles) and N-(3-dimethylaminopropyl)-N'-ethylcarbodiimide hydrochloride (0.133 g, 0.69 mmoles) and N-methylmorpholine (0.255 ml, 2.32 mmoles) then stirred at ambient temperature under a nitrogen atmosphere for 18 h. The mixture was washed with water (2×20 ml) and saturated brine (20 ml) then separated and dried over sodium sulphate, filtered and evaporated to dryness. The residue was chromatographed on silica gel eluting with an ethyl acetate/isohexane gradient. This gave the title compound as a colorless oil (0.184 g 76%).

$^1$H-NMR (CDCl$_3$, 300 MHz) δ 8.55 (d, J=6 Hz, 1H, ArH), 7.97 (s, 1H, ArH), 7.68-7.74 (m, 2H, 2× ArH), 7.66 (d, J=3 Hz, 1H, ArH), 7.22 (d, J=3 Hz, 1H, ArH), 6.69-6.79 (brs, 1H, NH), 4.57 (d, J=6 Hz, 2H, CH$_2$), 4.29 (d, J=7.5 Hz, 2H, CH$_2$), 3.98 (s, 2H, CH$_2$), 3.93 (s, 3H, CH$_3$), 2.09-2.24 (m, 1H, CH), 0.89 (d, J=8 Hz, 6H, 2×CH$_3$).

Example 60

Methyl 3-[(5-chloro-1-isobutyl-indazol-7-yl)methyl]imidazo[1,5-a]pyridine-7-carboxylate, Compound 60

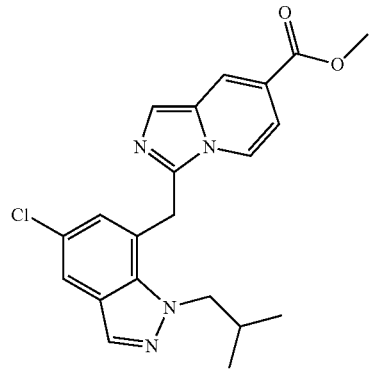 [SMILES: COC(=O)c1ccn2c(Cc3cc(Cl)cc4cnn(CC(C)C)c34)ncc2c1]

A solution/suspension of compound 59 (0.184 g, 0.44 mmol) in toluene was treated with phosphorus oxychloride (1 ml) and stirred at 90° C. under a nitrogen atmosphere for 22.5 h. The mixture was cooled and treated with water (20 ml) then neutralised by addition of solid sodium hydrogen carbonate. The mixture was then extracted with ethyl acetate (2×25 ml) and the organics separated and dried over sodium sulphate, filtered and evaporated to dryness. The residue was chromatographed on silica gel eluting with an ethyl acetate/isohexane gradient to give the title compound as a yellow oil (0.092 g, 52%).

$^1$H-NMR (CDCl$_3$, 300 MHz) δ 8.35 (s, 1H, ArH), 7.98 (s, 1H, ArH), 7.75 (s, 1H, ArH), 7.59-7.65 (m, 2H, 2× ArH), 7.15 (dd, J=2 and 7.5 Hz, 1H, ArH), 6.72 (d, J=2 Hz, 1H, ArH), 4.79 (s, 2H, CH$_2$), 4.32 (d, J=7.5 Hz, 2H, CH$_2$), 3.95 (s, 3H, CH$_2$), 2.15-2.31 (m, 1H, CH), 0.89 (d, J=8 Hz, 6H, 2×CH$_3$).

Example 61

3-[(5-Chloro-1-isobutyl-indazol-7-yl)methyl]imidazo[1,5-a]pyridine-7-carboxylic acid, Compound 61

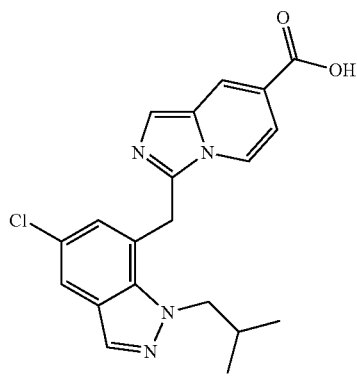 [SMILES: CC(C)Cn1ncc2cc(Cl)cc(Cc3ncc4cc(C(=O)O)ccn34)c21]

Compound 61 was prepared from compound 60 following general method 4. Yield: 67%.

$^1$H-NMR (CD$_3$OD, 300 MHz) δ 8.31 (s, 1H, ArH), 7.95 (d, J=7.5 Hz, 1H, ArH), 7.70 (s, 1H, ArH), 7.66 (d, J=2 Hz, 1H, ArH), 7.62 (s, 1H, ArH), 7.23 (dd, J=2 and 7.5 Hz, 1H, ArH), 6.77 (d, J=2 Hz, 1H, ArH), 4.85 (s, 2H, CH$_2$), 4.21 (d, J=7.5 Hz, 2H, CH$_2$), 2.06-2.24 (m, 1H, CH), 0.83 (d, J=8 Hz, 6H, 2×CH$_3$).

LC-MS: m/z 383 and 385 (M+H$^+$).

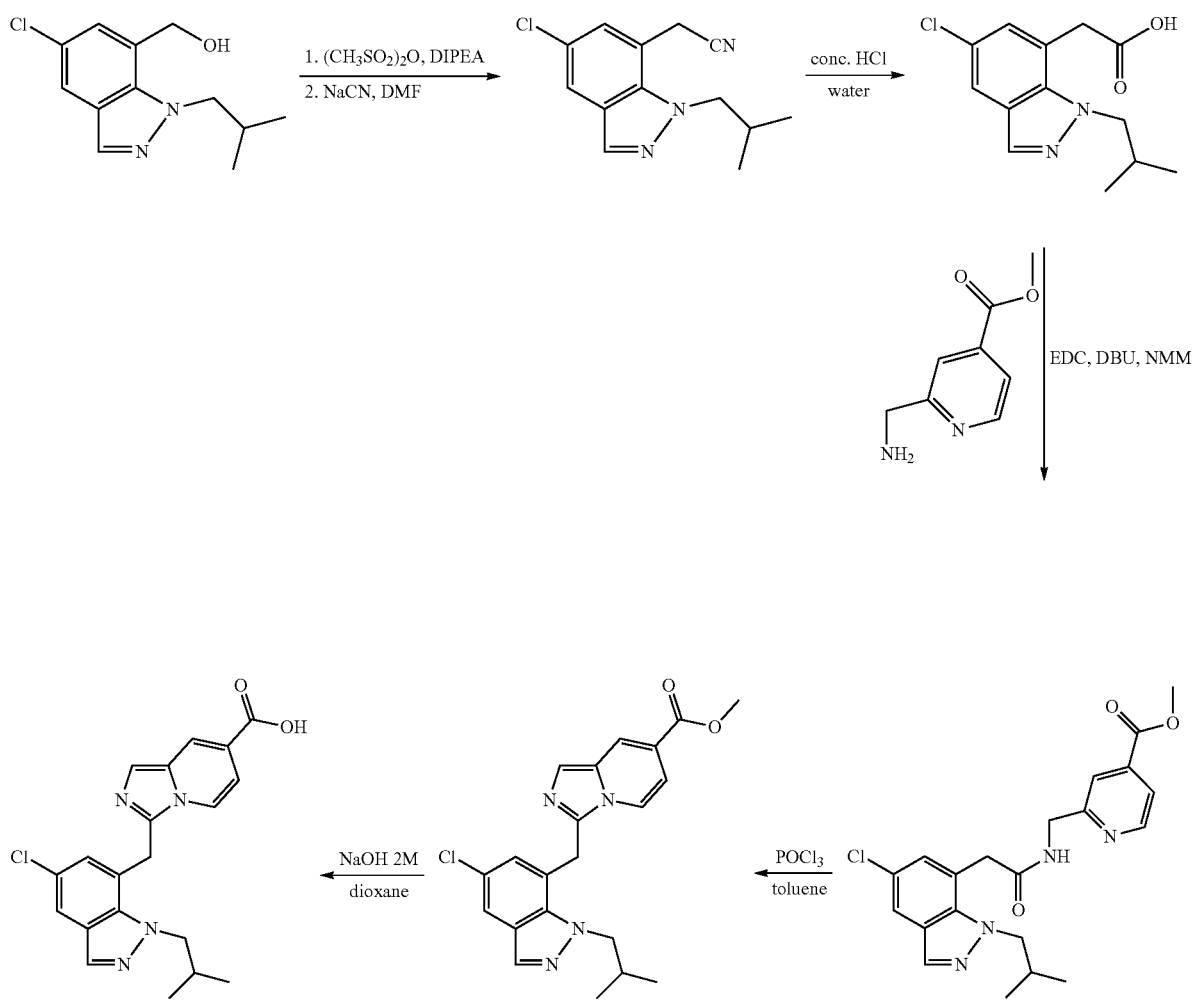

Scheme 3. Synthesis of compound 61

Example 62

5-bromo-2-amino-benzoicacetic acid, barium dimer, Compound 62

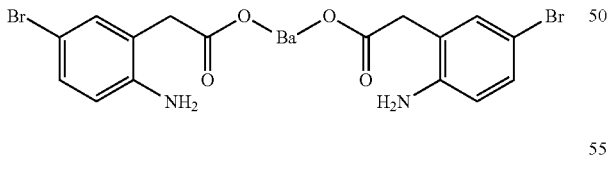

Example 63

7-Bromomethyl-5-chloro-1-isobutyl-1H-indazole, Compound 63

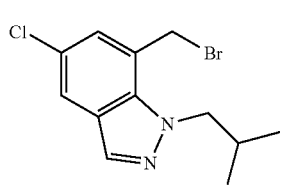 [SMILES: CC(C)Cn1ncc2cc(Cl)cc(CBr)c21]

To a suspension of 5-bromo-2-oxyindole in water was added barium hydroxide and the resulting mixture was heated at reflux for 16 h. Then, the reaction was cool down to 0° C. and conc. HCl was added to reach pH 8. The mixture was heated at reflux for 30', and then heated at 70° C. for 2 h followed by heating at 50° C. for 16 h.

The reaction was stopped, cooled down to 0° C. resulting in the precipitation of a solid that was collected by filtration and dried in a vacuum oven for 16 h.

To a solution of compound 17 (0.25 g, 1.05 mmol) in dichloromethane (10 mL) was added a 1M solution of PB$_3$ in dichloromethane (1.15 mL, 1.15 mmol) and the resulting mixture was stirred at r.t. for 16 h. Then, the reaction was quenched by adding water and diluted with more dichloromethane. The organic layer was separated, washed with Brine, dried (MgSO$_4$), filtered and the solvent was evaporated to give the title compound as a yellow oil. (0.263 g, 83%)

$^1$H-NMR (CDCl$_3$, 300 MHz) δ 7.99 (s, 1H, ArH), 7.69 (s, 1H, ArH), 7.32 (s, 1H, ArH), 4.79 (s, 2H, —CH$_2$Br), 4.48 (d, 2H, J=7.3 Hz, NCH), 2.29 (m, 1H, —CH(CH$_3$)$_2$), 0.98 (d, 6H, J=6.7 Hz, CH(CH$_3$)$_2$.

Example 64

5-Bromo-1-(5-chloro-1-isobutyl-1H-indazol-7-ylmethyl)-1,3-dihydro-indol-2-one, Compound 64

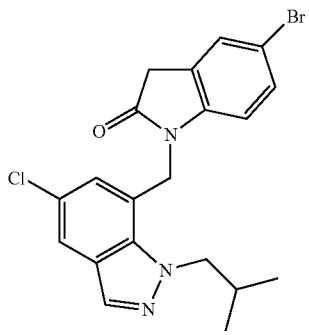 [SMILES: CC(C)Cn1ncc2cc(Cl)cc(CN3C(=O)Cc4cc(Br)ccc43)c21]

A mixture of compound 62 (0.78 g, 1.31 mmol) and compound 63 (0.263 g, 0.872 mmol) in tetrahydrofuran (9 mL) was heated at 110° C. under microwave conditions for 1 h. Then, the reaction mixture was filtered over Celite and the filtrate was concentrated to dryness under vacuum. Then, the residue was purified by chromatography column on a 20 g SPE cartridge to give the title compound as a colorless solid. (0.185 g, 49%)

$^1$H-NMR (CDCl$_3$, 300 MHz) δ 7.99 (s, 1H, ArH), 7.62 (s, 1H, ArH), 7.50 (s, 1H, ArH), 7.34 (d, 1H, J=8.9 Hz, ArH), 6.81 (s, 1H, ArH), 6.46 (d, 1H, J=8.9 Hz, ArH), 5.35 (s, 2H, ArCH$_2$N), 4.41 (d, 2H, J=7.3 Hz, NCH$_2$), 3.77 (s, 2H, NCOCH$_2$—), 2.32 (m, 1H, —CH(CH$_3$)$_2$), 0.98 (d, 6H, J=6.7 Hz, CH(CH$_3$)$_2$.

LC-MS: m/z 433 M+H$^+$

Example 65

1-(5-Chloro-1-isobutyl-1H-indazol-7-ylmethyl)-2-oxo-2,3-dihydro-1H-indole-5-carboxylic acid methyl ester, Compound 65

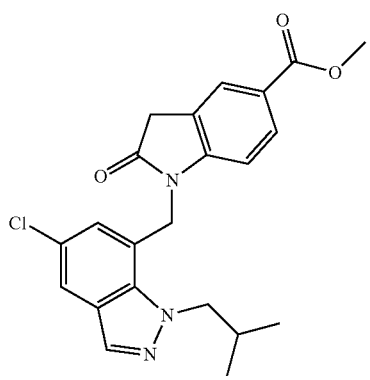 [SMILES: COC(=O)c1ccc2c(c1)CC(=O)N2Cc1cc(Cl)cc2cnn(CC(C)C)c12]

A mixture of compound 64 (0.1 g, 0.231 mmol), molybdenumhexacarbonyl (0.03 g, 0.115 mmol), Hermann's catalyst (0.022 g, 0.023 mmol), Xantphos (0.027 g, 0.0426 mmol), triethylamine (0.643 mL, 0.462 mmol) in a mixture of tetrahydrofuran (3 mL) and methanol (0.9 mL) was heated at 150° C. under microwave conditions for 10 minutes. Then, the reaction was quenched by adding water and diluted with ethyl acetate. The organic layer was separated, washed with Brine, dried (MgSO$_4$), filtered and the solvent was evaporated. Then, the residue was purified by chromatography column on a 20 g SPE cartridge to give the title compound as a colorless solid. (0.043 g, 45%)

$^1$H-NMR (CDCl$_3$, 300 MHz) δ 8.04 (s, 1H, ArH), 7.99 (s, 1H, ArH), 7.95 (d, 1H, J=8.9 Hz, ArH), 7.61 (s, 1H, ArH), 6.80 (s, 1H, ArH), 6.63 (d, 1H, J=8.9 Hz, ArH), 5.40 (s, 2H, ArCH$_2$N), 4.42 (d, 2H, J=7.3 Hz, NCH$_2$), 3.92 (s, 3H, —CO$_2$CH$_3$), 3.80 (s, 2H, NCOCH$_2$—), 2.34 (m, 1H, —CH(CH$_3$)$_2$), 0.98 (d, 6H, J=6.7 Hz, CH(CH$_3$)$_2$.

LC-MS: m/z 412 M+H$^+$

Example 66

1-(5-Chloro-1-isobutyl-1H-indazol-7-ylmethyl)-2-oxo-2,3-dihydro-1H-indole-5-carboxylic acid, Compound 66

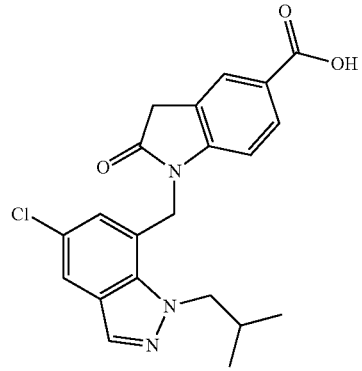 [SMILES: CC(C)Cn1ncc2cc(Cl)cc(CN3C(=O)Cc4cc(C(=O)O)ccc43)c21]

A mixture of compound 65 (0.021 g, 0.05 mmol), lithium hydroxide (0.09 g, 0.208 mmol) in a mixture of tetrahydrofuran (1.5 mL), water (0.5 mL) and methanol (0.5 mL) was heated at 100° C. under microwave conditions for 10 minutes. Then, the reaction was quenched by adding water and diluted with ethyl acetate. The organic layer was separated, washed with Brine, dried (MgSO$_4$), filtered and the solvent was evaporated.

Then, the residue was purified by chromatography column on a 20 g SPE cartridge to give the title compound as a colorless solid. (0.016 g, 80%)

$^1$H-NMR (CDCl$_3$, 300 MHz) δ 8.09 (s, 1H, ArH), 8.02 (d, 1H, J=8.9 Hz, ArH), 7.99 (s, 1H, ArH), 7.62 (s, 1H, ArH), 6.80 (s, 1H, ArH), 6.65 (d, 1H, J=8.9 Hz, ArH), 5.40 (s, 2H, ArCH$_2$N), 4.43 (d, 2H, J=7.3 Hz, NCH$_2$), 3.82 (s, 2H, NCOCH$_2$—), 2.34 (m, 1H, —CH(CH$_3$)$_2$), 0.87 (d, 6H, J=6.7 Hz, CH(CH$_3$)$_2$.

LC-MS: m/z 398 M+H$^+$

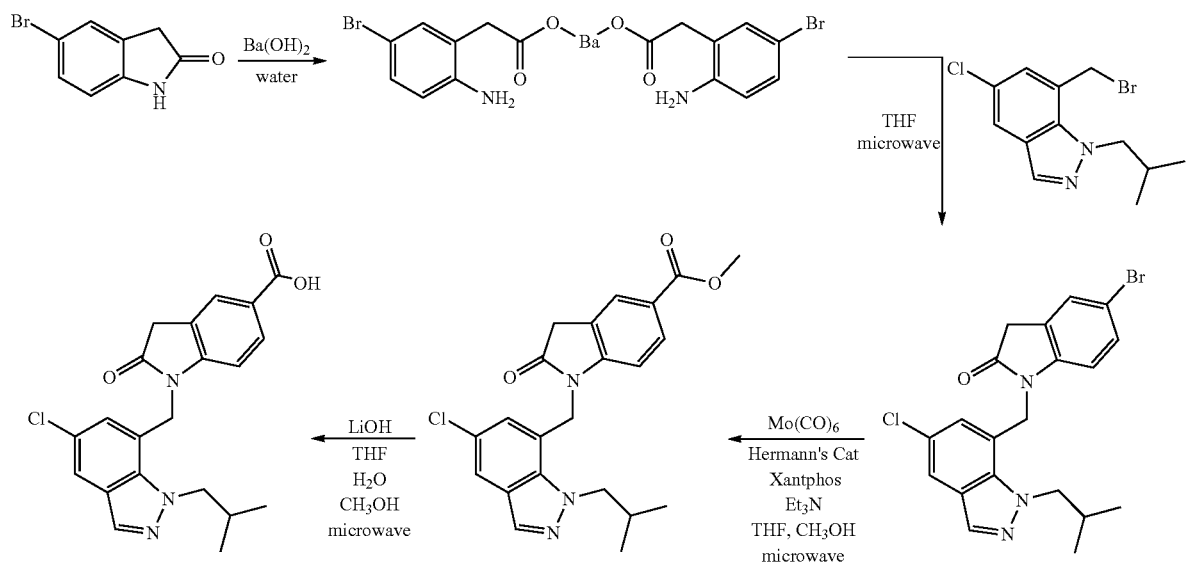

Scheme 4. Synthesis of compound 66

Example 67

Methyl 3-amino-1-[(5-chloro-1-isobutyl-indazol-7-yl)methyl]indazole-5-carboxylate, Compound 67

Example 68

3-Amino-1-[(5-chloro-1-isobutyl-indazol-7-yl)methyl]indazole-5-carboxylic acid, Compound 68

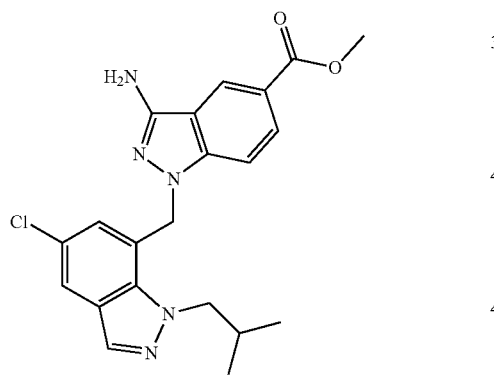

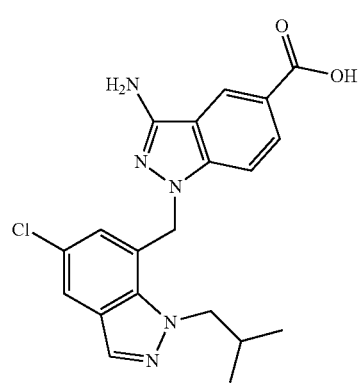 [SMILES: CC(C)Cn1ncc2cc(Cl)cc(Cn3nc(N)c4cc(C(=O)O)ccc43)c21]

A mixture of compound 17 (0.112 g, 0.47 mmol), methyl 3-amino-1H-indazole-5-carboxylate (0.075 g, 0.39 mmol), di-tert-butyl azocarboxylate (0.135 g, 0.59 mmol), triphenylphosphine (0.155 g, 0.59 mmol), in tetrahydrofuran (4 mL) was heated at 140° C. under microwave conditions for 20 minutes. Then, the reaction was quenched by adding water and diluted with ethyl acetate. The organic layer was separated, washed with Brine, dried (MgSO$_4$), filtered and the solvent was evaporated. Then, the residue was purified by chromatography column on a 20 g SPE cartridge to give the title compound as a colorless solid. (0.090 g, 56%)

$^1$H-NMR (CDCl$_3$, 300 MHz) δ 8.41 (s, 1H, ArH), 8.01 (dd, 1H, J=1.8, 9 Hz, ArH), 7.97 (s, 1H, ArH), 7.64 (d, 1H, J=1.8 Hz, ArH), 7.11 (d, 1H, J=9 Hz, ArH), 6.81 (s, 1H, ArH), 5.75 (s, 2H, ArCH$_2$N), 4.38 (d, 2H, J=7.3 Hz, NCH$_2$), 4.33 (bs, 2H, NH$_2$), 3.94 (s, 3H, —CO$_2$CH$_3$), 2.29 (m, 1H, —CH(CH$_3$)$_2$), 0.91 (d, 6H, J=6.7 Hz, CH(CH$_3$)$_2$.

LC-MS: m/z 412 M+H$^+$

A mixture of compound 67 (0.045 g, 0.11 mmol), lithium hydroxide (0.02 g, 0.44 mmol) in a mixture of tetrahydrofuran (2 mL), water (1 mL) and methanol (1 mL) was heated at 100° C. under microwave conditions for 10 minutes. Then, the reaction was quenched by adding water and diluted with ethyl acetate. The organic layer was separated, washed with Brine, dried (MgSO$_4$), filtered and the solvent was evaporated.

Then, the residue was purified by chromatography column on a 20 g SPE cartridge to give the title compound as a colorless solid. (0.026 g, 60%)

$^1$H-NMR (CH$_3$OD, 300 MHz) δ 8.55 (s, 1H, ArH), 8.01 (s, 2H, ArH), 7.69 (d, 1H, J=1.8 Hz, ArH), 7.26 (d, 1H, J=9 Hz, ArH), 6.78 (bs, 1H, ArH), 5.81 (s, 2H, ArCH$_2$N), 4.37 (d, 2H, J=7.3 Hz, NCH$_2$), 2.25 (m, 1H, —CH(CH$_3$)$_2$), 0.87 (d, 6H, J=6.7 Hz, CH(CH$_3$)$_2$.

LC-MS: m/z 398 M+H$^+$

Example 69

Methyl 1-[(5-chloro-1-isobutyl-indazol-7-yl)methyl]-3-(methylamino)indazole-5-carboxylate, Compound 69

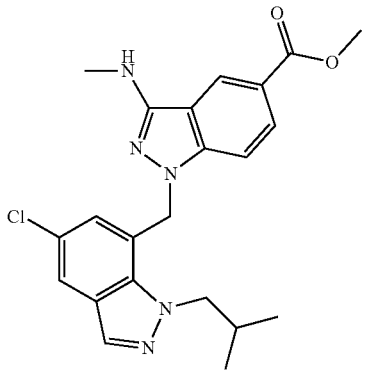 [SMILES: CNc1nn(Cc2cc(Cl)cc3cnn(CC(C)C)c23)c2ccc(C(=O)OC)cc12]

A mixture of compound 67 (0.054 g, 0.13 mmol), p-toluenesulphonic acid (0.003 g, 0.013 mmol), in trimethylorthoformate (3 mL) was heated at 100° C. in a closed vessel for 16 h. Then, the reaction was concentrated to dryness under vaccum. The residue was dissolved in tetrahydrofuran (4 mL), sodium borohydride was added (0.015 g, 0.395 mmol) and the resulting mixture was heated at 60° C. for 5 h.

The reaction was stopped and let to cool down. Then it was quenched slowly by adding water followed by adding ethyl acetate. The organic layer was separated, washed with Brine, dried ($MgSO_4$), filtered and the solvent was evaporated. Then, the residue was purified by chromatography column on a 20 g SPE cartridge to give the title compound as a colorless solid. (0.022 g, 40%)

$^1$H-NMR ($CDCl_3$, 300 MHz) δ 8.36 (s, 1H, ArH), 7.97 (s, 1H, ArH), 7.96 (dd, 1H, J=1.8, 9 Hz, ArH), 7.64 (d, 1H, J=1.8 Hz, ArH), 7.01 (d, 1H, J=9 Hz, ArH), 6.86 (s, 1H, ArH), 5.79 (s, 2H, ArCH$_2$N), 4.46 (d, 2H, J=7.3 Hz, NCH$_2$), 3.94 (s, 3H, —CO$_2$CH$_3$), 3.11 (s, 3H, NCH$_3$), 2.33 (m, 1H, —CH(CH$_3$)$_2$), 0.94 (d, 6H, J=6.7 Hz, CH(CH$_3$)$_2$.

LC-MS: m/z 426 M+H$^+$

Example 70

1-[(5-Chloro-1-isobutyl-indazol-7-yl)methyl]-3-(methylamino)indazole-5-carboxylic acid, Compound 70

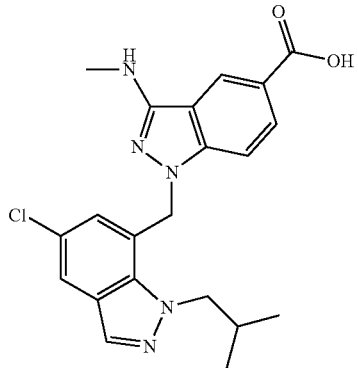 [SMILES: CNc1nn(Cc2cc(Cl)cc3cnn(CC(C)C)c23)c2ccc(C(=O)O)cc12]

A mixture of compound 69 (0.021 g, 0.05 mmol), lithium hydroxide (0.09 g, 0.2 mmol) in a mixture of tetrahydrofuran (1 mL), water (0.5 mL) and methanol (0.5 mL) was heated at 100° C. under microwave conditions for 10 minutes. Then, the reaction was quenched by adding water and diluted with ethyl acetate. The organic layer was separated, washed with Brine, dried ($MgSO_4$), filtered and the solvent was evaporated.

Then, the residue was purified by chromatography column on a 20 g SPE cartridge to give the title compound as a colorless solid. (0.015 g, 70%)

$^1$H-NMR ($CH_3OD$, 300 MHz) δ 8.36 (s, 1H, ArH), 7.92 (m, 2H, ArH), 7.58 (d, 1H, J=1.8 Hz, ArH), 6.91 (d, 1H, J=9 Hz, ArH), 6.74 (bs, 1H, ArH), 5.72 (s, 2H, ArCH$_2$N), 4.39 (d, 2H, J=7.3 Hz, NCH$_2$), 2.25 (m, 1H, —CH(CH$_3$)$_2$), 0.87 (d, 6H, J=6.7 Hz, CH(CH$_3$)$_2$.

LC-MS: m/z 412M+H$^+$

The above compounds were tested for PG antagonist activity as follows using human recombinant prostanoid receptor (DP$_1$, EP$_{1-4}$, FP, IP and TP) stable cell lines:

In order to measure the response of $G_s$ and $G_i$ coupled prostanoid receptors as a $Ca^{2+}$ signal, chimeric G protein cDNAs were used. Stable cell lines over-expressing human prostanoid DP$_1$, EP$_{1-4}$, FP, IP, and TP receptors were established as follows:

Briefly, human prostanoid DP$_1$, EP$_2$, and EP$_4$ receptor cDNAs were co-transfected with chimeric $G_{qs}$ cDNA containing a haemagglutanin (HA) epitope; human prostanoid EP$_3$ receptors were co-transfected with chimeric $G_{qi}$-HA; human EP$_1$, FP, IP, and TP receptor cDNAs were expressed with no exogenous G-proteins. $G_{qs}$ and $G_{qi}$ chimeric cDNAs (Molecular Devices, Sunnyvale, Calif., U.S.A.), as well as cDNAs of prostanoid receptors, were cloned into a pCEP$_4$ vector with a hygromycin B selection marker. Transfection into HEK-293 EBNA (Epstein-Barr virus nuclear antigen) cells was achieved by the FuGENE 6 transfection Reagent (Roche Applied Science, Indianapolis, Ind., USA). Stable transfectants were selected according to hygromycin resistance. Because $G_{qs}$ and $G_{qi}$ contained an HA epitope, G-protein expression was detected by Western blotting analysis using anti-mouse HA monoclonal antibody and horseradish peroxidase (HRP)-conjugated secondary antibody, while functional expression of prostanoid receptors was detected by FLIPR screening (Matias et al., 2004). These stable cell lines were validated using previously published antagonists at 10 μM against serial dilutions of standard agonists by FLIPR functional assays for $Ca^{2+}$ Signaling (as described below).

$Ca^{2+}$ signaling studies were performed using a FLIPR TETRA system (Molecular Devices, Sunnyvale, Calif., USA) in the 384-format. This is a high-throughput instrument for cell-based assays to monitor $Ca^{2+}$ signaling associated with GPCRs and ion channels. Cells were seeded at a density of $5 \times 10^4$ cells/well in BioCoat poly-D-lysine coated, black wall, clear bottom 384-well plates (BD Biosciences, Franklin lakes, NJ, USA) and allowed to attach overnight in an incubator at 37° C. The cells were then washed twice with HBSS-HEPES buffer (Hanks' balanced salt solution without bicarbonate and phenol red, 20 mM HEPES, pH 7.4) using an EL×405 Select CW Microplate Washer (BioTek, Winooski, Vt., USA). After 60 min of dye-loading in the dark using the $Ca^{2+}$-sensitive dye Fluo-4AM (Invitrogen, Carlsbad, Calif., USA), at a final concentration of $2 \times 10^{-6}$M, the plates were washed 4 times with HBSS-HEPES buffer to remove excess dye and leaving 50 μl of buffer in each well. The plates were then placed in the FLIPR TETRA instrument and allowed to equilibrate at 37° C. AGN-211377 was added in a 25 μl volume to each well to give final concentrations of 0.4 μM, 0.3 μM, 10 μM, and 30 μM; or 0.067 μM, 0.4 μM, 0.3 μM, 0.67 μM, and 1 μM for cells over-expressing TP receptors. After 4.5 minutes, a 7-point serial dilution of the standard agonist for the corresponding receptor, in a 25 μl volume was injected at the final concentrations from $10^{-11}$ M to $10^{-5}$ M in 10-fold serial dilution increments for cells expressing human recombinant $DP_1$, $EP_1$, $EP_2$, $EP_3$, $EP_4$, FP, and IP receptors. The dose range for the standard agonist for human recombinant TP receptors was from $10^{-12}$M to $10^{-6}$M. HBSS-HEPES buffer was used as the negative control for the standard agonists. Cells were excited with LED (light emitting diode) excitation at 470-495 nm and emission was measured through an emission filter at 515-575 nm. Assay plates were read for 3.5 minutes using the FLIPR$^{TETRA}$. The peak increase in fluorescence intensity was recorded for each well. On each plate, negative controls, dose response of positive controls, and co-treatments of antagonist-agonist for each dose were in triplicates. Standard agonists were as follows: DP=BW 245C, $EP_1$-$EP_4$=$PGE_2$, FP=17-phenyl-$PGF_{2\alpha}$, IP=Cicaprost, and TP=U-46619. The peak fluorescence change in each well containing drug was expressed relative to vehicle controls with the standard agonist at $10^{-6}$M (the positive control). To obtain concentration-response curves, compounds were tested in triplicate in each plate over the desired concentration range.

$Ca^{2+}$ Signal Studies on Human Recombinant Prostanoid Receptor $DP_2$

FLIPR functional assays were conducted at Millipore to monitor the activity anti-asthmatic against human $DP_2$ receptors stably expressed in the Chem-5 proprietary host cell line generated by Millipore. Prior to standard agonist addition, the compounds were spotted at 10 μM along with vehicle control (1% Ethanol in HBSS-HEPES buffer) across the assay wells. The assay plate was incubated at room temperature for 10 minutes in the dark. Then an 8-point serial dilution dose response from $10^{-12}$M to $10^{-5}$M of the standard agonist $PGD_2$ was performed. Assay plates were read for 90 seconds using the FLIPR$^{TETRA}$. The fluorescence measurements were collected to calculate $IC_{50}$ values. The assays were done at least 3 times to give n=3.

Data Processing

All plates were subjected to appropriate baseline corrections. Maximum fluorescence values were exported. The raw data of n=1 was first processed by Activity Base using non-linear regression curve fit to calculate the percentage activity of each data point relative to the positive control (=$10^{-6}$M of the standard agonist). Then n=3 of this data were exported to GraphPad Prism 4 to calculate the average $EC_{50}$ of the standard agonist, and the $IC_{50}$ (the concentration of the antagonist required to inhibit half the standard agonist activity) were calculated using nonlinear regression curve fit, with constraints of bottom constant equal to 0 and top constant equal to 100. Calculation of Kb=[Antagonist Concentration]/($IC_{50}$/$EC_{50}$-1). When no antagonism was detected or when Kb≥10,000 nM, the antagonist is defined as not active (NA).

| FLIPR data | | | | | | | | |
|---|---|---|---|---|---|---|---|---|
| Compound Number | FP | DP1 | EP1 | EP2 | EP3 | EP4 | IP | TP |
| 41 | 70 | 460 | 730 | 9200 | NA | 24 | NA | 40 |
| 42 | 40 | 590 | 2300 | NA | NA | 22 | NA | 160 |
| 43 | 700 | 1700 | NA | NA | NA | 100 | NA | 450 |
| 44 | 150 | 1000 | 1500 | PAg | NA | 28 | PAg | Ag |
| 45 | 80 | 300 | 800 | NA | NA | 5 | Ag | Ag |
| 46 | 200 | NA | 3000 | NA | NA | 330 | NA | 1400 |
| 47 | 3000 | 1400 | 500 | 5000 | NA | 1700 | 1000 | 700 |
| 48 | 500 | 5500 | NA | NA | NA | 130 | NA | 740 |
| 49 | 1900 | 3500 | 9800 | NA | NA | 90 | 8900 | 170 |
| 50 | NA | NA | NA | NA | NA | 80 | NA | 5000 |
| 51 | 4900 | NA | NA | NA | NA | 280 | 8000 | 280 |

-continued

| FLIPR data | | | | | | | | |
|---|---|---|---|---|---|---|---|---|
| Compound Number | FP | DP1 | EP1 | EP2 | EP3 | EP4 | IP | TP |
| 52 | 700 | Ag | 600 | NA | 3400 | 90 | 5500 | 20 |
| 53 | 70 | 640 | 5700 | NA | NA | 90 | NA | 1000 |
| 54 | 600 | 200 | NA | NA | NA | 380 | 9500 | 1600 |
| 55 | 3000 | NA | 4000 | NA | NA | 80 | 8900 | Ag |
| 56 | NA | 5200 | 9000 | NA | NA | 6 | 9000 | 30 |
| 61 | 600 | 4700 | NA | NA | NA | 200 | NA | NA |
| 68 | 35 | 3700 | NA | NA | NA | 60 | 9300 | 1300 |
| 70 | 17 | 1000 | 2300 | 7000 | 8100 | 1 | 900 | 300 |

PAg = partial agonist, Ag = agonist, NA = not active

As shown in TABLE 1, the preferred compounds of this invention are pan antagonists having activity at the FP, DP, $EP_1$, $EP_4$ and TP receptors, many are inactive at the $EP_2$ and $EP_3$ receptors. Thus, these compounds have a biological selectivity profile making them useful in treating diseases and conditions which are mediated by FP, DP, $EP_1$, $EP_4$ and TP receptors, without the side effects mediated by IP and $EP_3$ receptors. Moreover, open $EP_2$ and IP receptors may impart additional therapeutic benefit, with particular respect to inflammatory diseases and diseases with an inflammatory component.

Thus, the compounds of this invention compound may be administered to treat $DP_1$, FP, $EP_1$, TP and/or $EP_4$ receptor mediated diseases or conditions.

For example, said condition or disease may be related to inflammation, or said $DP_1$, FP, $EP_1$, TP and/or $EP_4$ receptor mediated condition or disease may be selected from the group consisting of allergic conditions, asthma, allergic asthma, allergic rhinitis, uveitis and related disorders, atherosclerosis, blood coagulation disorders, bone disorders, cancer, cellular neoplastic transformations, chronic obstructive pulmonary diseases and other forms of lung inflammation, congestive heart failure, diabetic retinopathy, diseases or conditions requiring a treatment of anti-coagulation, diseases requiring control of bone formation and resorption, fertility disorders, gangrene, glaucoma, hyperpyrexia, immune and autoimmune diseases, inflammatory conditions, metastic tumor growth, migraine, mucus secretion disorders, nasal congestion, nasal inflammation, occlusive vascular diseases, ocular hypertension, ocular hypotension, osteoporosis, rheumatoid arthritis, pain, perennial rhinitis, pulmonary congestion, pulmonary hypotension, Raynaud's disease, rejection in organ transplant and by-pass surgery, respiratory conditions, hirsutism, rhinorrhea, shock, sleep disorders, and sleep-wake cycle disorders.

Said compound may be administered as a surgical adjunct in ophthalmology for cataract removal and artificial lens insertion, ocular implant procedures, photorefractive radial keratotomy and other ophthalmological laser procedures or as a surgical adjunct in a procedure involving skin incisions, relief of pain and inflammation and scar formation/keloids post-surgery, for treating sports injuries and general aches and pains in muscles and joints.

Preferably, said $DP_1$, FP, $EP_1$, TP, and/or $EP_4$ receptor mediated condition or disease is an $EP_1$ and/or $EP_4$ receptor mediated condition or disease.

Preferably, said $DP_1$, FP, $EP_1$, TP and/or $EP_4$ receptor mediated condition or disease is an allergic condition, e.g. a dermatological allergy, or an ocular allergy, or a respiratory allergy, e.g. nasal congestion, rhinitis, and asthma.

Said condition or disease may be related to pain.

Said condition or disease characterized by fibrosis

Said condition or disease may be selected from the group consisting of arthritis, migraine, and headache.

Said condition or disease may be associated with the gastrointestinal tract, wherein said condition or disease may be peptic ulcer, heartburn, reflux esophagitis, erosive esophagitis, non-ulcer dyspepsia, infection by *Helicobacter pylori*, alrynitis, and irritable bowel syndrome.

Said condition or disease may be selected from the group consisting of hyperalgesia and allodynia, or said condition or disease may be related to mucus secretion, wherein said mucus secretion is gastrointestinal, or occurs in the nose, sinuses, throat, or lungs.

Said condition or disease is related to abdominal cramping, e.g. said condition or disease may be irritable bowel syndrome.

Said condition or disease may be a bleeding disorder, or a sleep disorder, or mastocytosis.

Said condition or disease may be associated with elevated body temperature, or ocular hypertension and glaucoma, or ocular hypotension.

Said condition may relate to surgical procedures to treat pain, inflammation and other unwanted sequelae wherein said surgical procedure includes incision, laser surgery or implantation.

The present invention also relates to a method of treating inflammation resulting from inflammatory diseases characterized by monocytic infiltration caused by the secretion of cytokines and/or chemokines by administration, to a patient in need of said treatment, of a pharmaceutical composition comprising a compound of the present invention The current finding that the compounds of this invention are effective in attenuating the production of TNF family cytokines (TNFα), and the classical interleukin-1 (IL-1) family cytokines is especially important. These cytokines exert a broad spectrum of biological and pathological effects. They play key roles in inflammation and RA pathogenesis by stimulating the release of multiple proinflammatory cytokines, including themselves, through the NFκB signaling pathway. Although alleviating the symptoms of RA in 50-65% of patients, a TNFα antibody is very expensive to use compared to chemically synthesized small molecules, inconvenient to administer usually requiring injections, and has been linked to tuberculosis, lymphoma, and other adverse effects. Unlike a TNFα antibody that totally eliminates all circulating TNFα in the system; the compounds of this invention only attenuate the production of TNFα by inhibiting proinflammatory PG receptors. Therefore the adverse effects associated with a TNFα antibody in elevating infectious and cancerous tendency is less likely.

Proinflammatory elements TNF, RANTES, and MCP-1 are involved in the cascade of events in the early and late stages of atherosclerosis. Plasma MCP-1 levels have been linked to cardiovascular disease risk factors in clinical studies. Platelet activation leads to the release of MIP-1α, RANTES, and IL-8, which attract leukocytes and further activate other platelets. These evidences provide a direct linkage between homeostasis, infection, and inflammation and the development of atherosclerosis. The compounds of this invention are able to target multiple biomarkers of inflammation, thrombosis, and atherothrombosis simultaneously, which may confer pharmaceutical potential on the compounds of this invention in treating atherosclerosis and atherothrombosis. As a result, the compounds of this invention are unlikely to be associated with cardiovascular liability as in the case of the COXIBs, conversely it may even have a beneficial effect on cardiovascular function.

In summary, because of their ability to suppress the synthesis of some key proinflammatory cytokines/chemokines IL-8, MCP-1, MDC, RANTES, and TNFα, the compounds of the present invention are not only at least as effective as COXIBs and NSAIDs in RA treatment, but also are a safer therapy in RA treatment. They are also a potential therapy for cardiovascular diseases.

The compounds of this invention treat or prevent inflammation at least in part by the decreasing the amount of the secretion of certain cytokines and/or chemokines that result from the exposure of the patient to a stimulant. In particular, the secretion of VEGF, MIP-1β, IL-8, MCP-1, MDC, and RANTES is reduced in those instances where said secretions are triggered by lipopolysaccharides (LPS) and or TNFα.

Interleukin-8 (IL-8): functions as a potent chemoattractants and activator of neutrophils, IL-8 is produced in response to stimulation with either IL-1 or TNFα. IL-8 not only accounts for a significant proportion of the chemotactic activity for neutrophils in rheumatoid arthritis (RA) synovial fluids, but also is a potent angiogenic factor in the RA synovium.

Monocyte chemoattractant protein-1 (MCP-1, or CCL-2): is not only believed to play a role in inflammatory diseases characterized by monocytic infiltration, such as RA rheumatoid arthritis, psoriasis, and atherosclerosis, but is also implicated in other diseases, such as atopic dermatitis, renal disease, pleurisy, allergy and asthma, colitis, endometriosis, polymyositis and dermatomyositis, uveitis, restenosis, brain inflammation and obesity. MCP-1 also controls leukocyte trafficking in vascular cells involved in diabetes and diabetes-induced atherosclerosis. MCP-1 antibodies are potential therapeutic agents for treating MCP-1/CCR2-mediated multiple inflammatory diseases.

Tumor necrosis factor α (TNFα): mainly secreted by macrophages and recognized for its importance in activating the cytokine cascade. TNFα stimulates the production of proinflammatory cytokines/chemokines, collagenases, metalloproteinases, and other inflammatory mediators; activates endothelial cells and neutrophils; promotes T- and B-cell growth, as well as stimulating bone resorption. The TNFα antibody infliximab not only decreases the production of local and systemic proinflammatory cytokines/chemokines, but also reduces serum MMP-3 production, nitric oxide synthase activity, VEGF release, and angiogenesis in inflamed joints.

Macrophage-derived chemokine (MDC) induces chemotaxis for monocyte-derived dendritic cells, activated T cells and natural killer (NK) cells (Ho et al., 2003). Highly expressed by the three major cell types involved in allergic inflammation: eosinophils, basophils, and Th2 lymphocytes (Garcia et al., 2005), as well as highly expressed in atopic dermatitis (Pivarcsi et al., 2005), MDC plays a role in inflammatory diseases such as allergic asthma and atopic dermatitis (Ho et al., 2003). Significantly enhanced in keratinocytes of patients with atopic dermatitis, MDC could be a candidate therapeutic target for inflammatory skin disease such as atopic dermatitis (Qi et al., 2009). MDC is also implicated in disease activity of RA. After combination treatment with the disease-modifying anti-rheumatic drugs leflunomide and methotrexate in RA patients, plasma MCP-1 and MDC concentrations were significantly lower, and so was the recruitment of inflammatory cells into the sites of inflammation (Ho et al., 2003). Moreover, MDC also amplify platelet activation and has been associated with the pathogenesis of atherosclerotic disease including thrombosis (Gleissner et al., 2008).

Regulated on Activation, Normal T Cell Expressed and Secreted (RANTES) is a chemoattractant for blood monocytes, memory T-helper cells and eosinophils, and plays an active role in recruiting leukocytes into inflammatory sites. It also stimulates the release of histamine from basophils, activates eosinophils and causes hypodense eosinophils, which is associated with diseases such as asthma and allergic rhinitis. RANTES receptor CCR5 is also expressed on cells involved in atherosclerosis (e.g. monocytes/macrophages, T lymphocytes, or Th1-type cells), and is specialized in mediating RANTES-triggered atherosclerotic plaque formation (Zernecke et al., 2008). Like MCP-1, stimulation with RANTES enhances production of IL-6 and IL-8 in RA fibroblast-like synovial cells; elevated MMP-3 production by chondrocytes, and inhibited proteoglycan synthesis and enhanced proteoglycan release from the chondrocytes (Iwamoto et al., 2008). Both MCP-1 and RANTES were found to play an important role in allergic lung inflammation, lung leukocyte infiltration, bronchial hyper-responsiveness, and the recruitment of eosinophils in the pathogenesis of asthma (Conti et al., 2001). Similar to MCP-1, RANTES also enhances the inflammatory response within the nervous system, which plays an apparent role in the pathogenesis of multiple sclerosis (Conti et al., 2001) Inhibitors for RANTES may provide clinical benefits in treating inflammation, CNS disorders, parasitic disease, cancer, autoimmune and heart diseases (Castellani et al., 2007).

The compounds of the present invention wherein said product is packaged and labelled for the treatment or prevention of a disease or condition selected from the group consisting of uveitis, allergic conditions, asthma, allergic asthma, allergic rhinitis, atherosclerosis, blood coagulation disorders, bone disorders, cancer, cellular neoplastic transformations, chronic obstructive pulmonary diseases and other forms of lung inflammation, congestive heart failure, diabetic retinopathy, diseases or conditions requiring a treatment of anticoagulation, diseases requiring control of bone formation and resorption, fertility disorders, hyperpyrexia, gangrene, glaucoma, hypothermia, immune and autoimmune diseases, inflammatory conditions, metastic tumor growth, migraine, mucus secretion disorders, nasal congestion, nasal inflammation, occlusive vascular diseases, ocular hypertension, ocular hypotension, osteoporosis, pain, perennial rhinitis, pulmonary congestion, pulmonary hypotension, Raynaud's disease, rejection in organ transplant and by-pass surgery, respiratory conditions, rheumatoid arthritis, rhinorrhea, shock, sleep disorders, sleep-wake cycle disorders, sports injuries, muscle aches and pains, and surgical adjunct for minimizing pain, inflammation and scar/keloid formation.

Those skilled in the art will readily understand that for administration the compounds disclosed herein can be admixed with pharmaceutically acceptable excipients which, per se, are well known in the art. Specifically, a drug to be administered systemically, it may be formulated as a powder, pill, tablet or the like, or as a solution, emulsion, suspension, aerosol, syrup or elixir suitable for oral or parenteral administration or inhalation.

For solid dosage forms, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glycerol monostearate or glycerol distcarate may be employed. They may also be coated by the technique described in the U.S. Pat. Nos. 4,256, 108; 4,166,452; and 4,265,874, which are hereby incorporate by reference in their entireties, to form osmotic therapeutic tablets for control release. Liquid pharmaceutically administrable dosage forms can, for example, comprise a solution or suspension of one or more of the compounds of the present invention and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, subcutaneously, intramuscularly or intravenously. Injectable formulations can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds of the present invention administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds is preferably in the range of about 0.5 ng/kg/day or about 1 ng/kg/day to about 100 mg/kg/day.

For ophthalmic application, solutions are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methylcellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthamologically acceptable tonicity adjustor.

Various buffers and means for adjusting pH may be used so long as the resulting preparation is ophthamologically acceptable. Accordingly, buffers include acetate buffers, citrate buffers, phosphate buffers and borate buffers. Acids or bases may be used to adjust the pH of these formulations as needed.

Similarly, an ophthamologically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

For topical use, creams, ointments, gels, solutions or suspensions, etc., containing the compound of the present invention are employed. Topical formulations may generally be comprised of a pharmaceutical carrier, cosolvent, emulsifier, penetration enhancer, preservative system, and emollient.

The actual dose of the compounds of the present invention depends on the specific compound, and on the condition to be treated; the selection of the appropriate dose is well within the knowledge of the skilled artisan.

A skilled person will also realize that the compounds of the present invention can be used in the manufacture of a medicament for the treatment of the disorders mentioned herein (e.g. the $DP_1$, FP, $EP_1$, TP and/or $EP_4$ receptor mediated diseases or conditions mentioned herein).

Patents and publications mentioned in the specification are indicative of the levels of those skilled in the art to which the invention pertains. These patents and publications are incorporated herein by reference to the same extent as if each individual application or publication was specifically and individually incorporated herein by reference.

The present invention is not to be limited in scope by the exemplified embodiments, which are only intended as illustrations of specific aspects of the invention. Various modifications of the invention, in addition to those disclosed herein, will be apparent to those skilled in the art by a careful reading of the specification, including the claims, as originally filed. It is intended that all such modifications will fall within the scope of the appended claims.

What is claimed is:
1. A compound of formula (I):

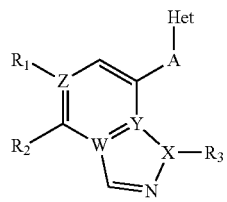
(I)

wherein:
A is selected from the group consisting of $C_1$-$C_3$ alkylene and CO;
X is either CH or N, wherein:
when X is CH, $R_3$ is selected from the group consisting of:

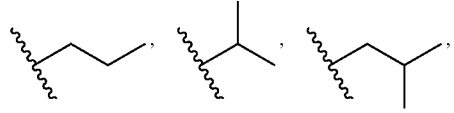

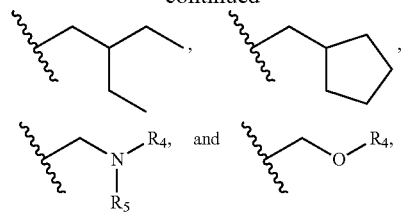

and when X is N, $R_3$ is selected from the group consisting of:

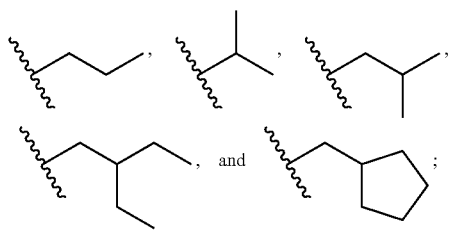

W and Y are either C or N;
Z is either C or N, wherein:
when Z is C, $R_1$ is selected from the group consisting of $C_1$-$C_3$ alkyl, $C_1$-$C_3$ haloalkyl, $CH_2OCH_3$, F, Cl, Br, halogen, $OCF_3$, $OCCl_3$, $OCBr_3$ and wherein $C_1$-$C_3$ alkyl may be optionally substituted by hydroxyl, halogen, amine and functional amines,
and when Z is N, there is no $R_1$ substituent;
$R_2$ is selected from the group consisting of H, $C_1$-$C_3$ alkyl, $C_1$-$C_3$ haloalkyl, $CH_2OCH_3$, F, Cl, Br, halogen, and $OCF_3$;
$R_4$ and $R_5$ are independently selected from the group consisting of $C_1$-$C_3$ alkyl and substituted $C_1$-$C_3$ alkyl, and when $R_3$ is

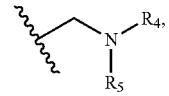

$R_4$ and $R_5$ can be joined to form a $C_3$-$C_6$ cycloalkyl;
Het is selected from the group consisting of:

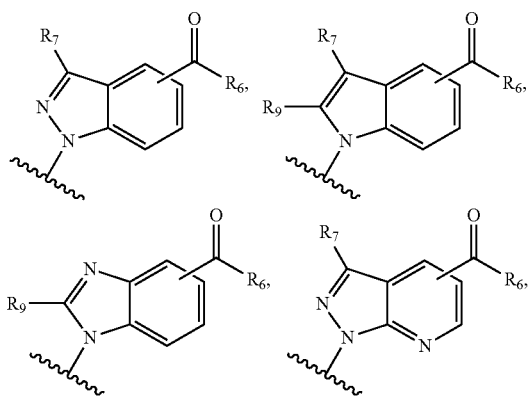

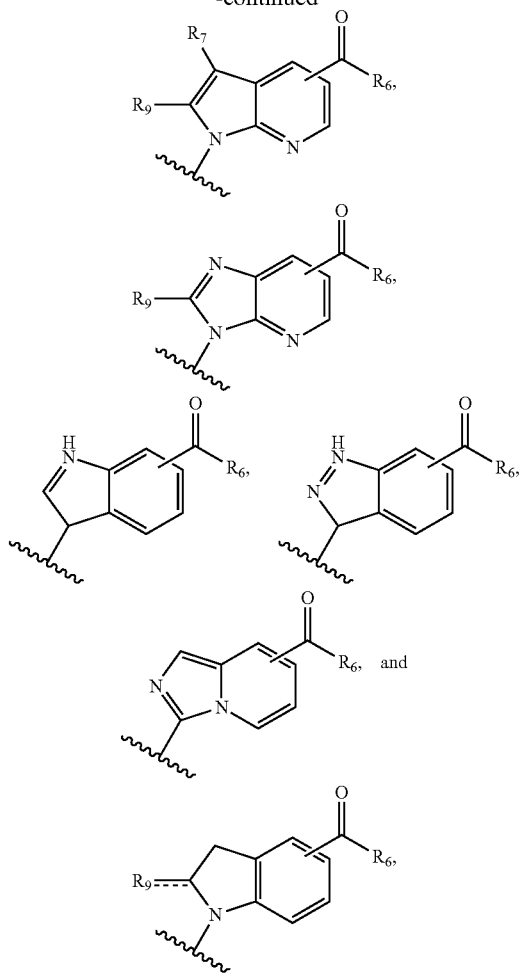

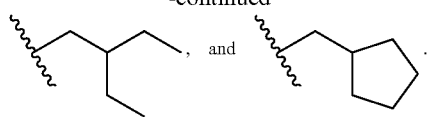

wherein:
R$_6$ is selected from the group consisting of OH, OCH$_3$, OCH(CH$_3$)$_2$, and NHSO$_2$R$_8$;
R$_7$ is selected from the group consisting of H, CH$_3$, CH$_2$CH$_3$, OCH$_3$, CH$_2$OH, CH$_2$OCH$_3$, NH$_2$, C$_1$-C$_3$ alkylamino, and C$_1$-C$_3$ dialkylamino;
R$_8$ is selected form the group consisting of C$_1$-C$_3$ alkyl and substituted C$_1$-C$_3$ alkyl; and,
R$_9$ is selected from the group consisting of O, OH, CH$_3$, halogen and OCH$_3$ the dashed bond represents the presence of a single or double bond;

and wherein the compounds can be in the form of a tautomer, a racemate, an enantiomer, a diastereomer, or a pharmaceutically acceptable salt.

2. The compound of claim 1, wherein A is C$_1$-C$_3$ alkyl.
3. The compound of claim 1, wherein A is CO.
4. The compound of claim 2, wherein A is CH$_2$.
5. The compound of claim 1, wherein Z is C and X is N.
6. The compound of claim 5, wherein R$_3$ is selected from group consisting of:

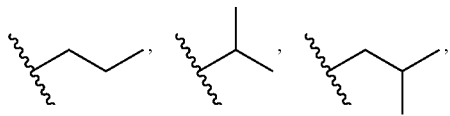

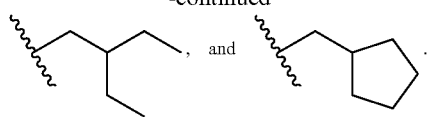

7. The compound of claim 6, where R$_1$ is halogen.
8. The compound of claim 6, wherein R$_2$ is H.
9. The compound of claim 1, wherein Het is selected from the group consisting of:

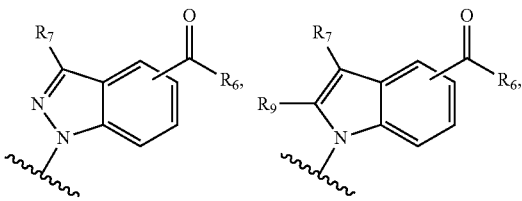

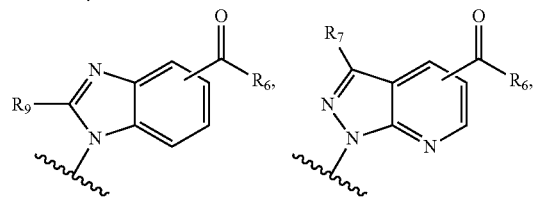

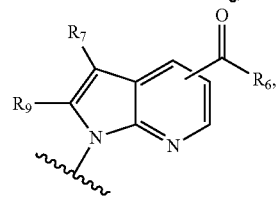

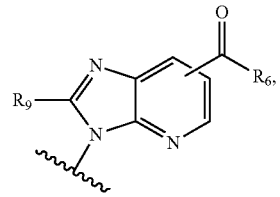

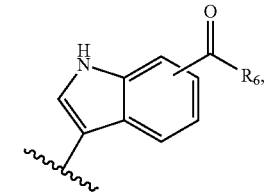

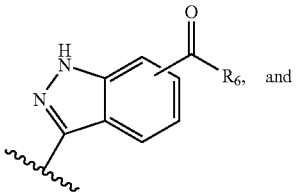

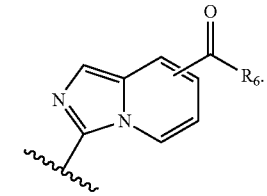

10. The compound of claim 9, wherein Het is:

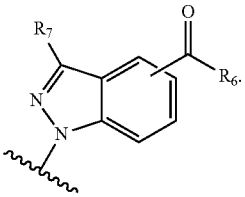

11. The compound of claim 9 wherein Het is:

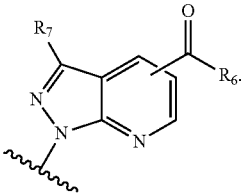

12. The compound of claim 1 wherein Z is C, $R_1$ is Cl or Br and $R_7$ is H or $NCH_3$.

13. The compound of claim 12 wherein X is N, $R_6$ is OH and $R_3$ is

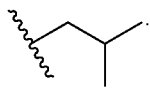 [SMILES: *CC(C)C]

14. The compound of claim 13 selected from the group consisting of

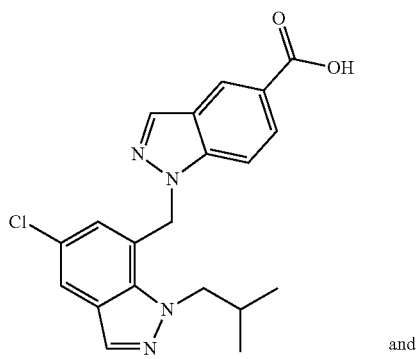

and

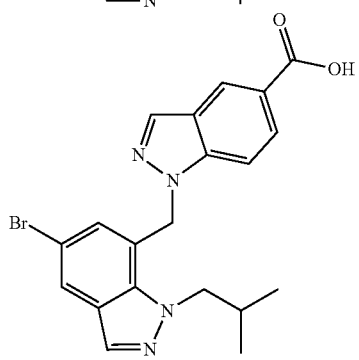

and

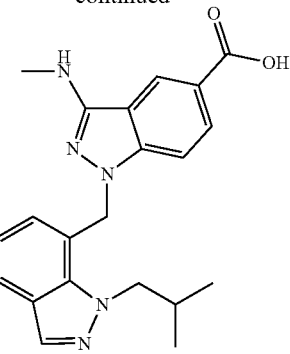

or a pharmaceutically acceptable salt thereof.

15. The compound of claim 1 selected from the group consisting of:
- 1-(5-Chloro-1-isobutyl-1H-indazol-7-ylmethyl)-1H-indazole-5-carboxylic acid;
- 1-(5-Bromo-1-isobutyl-1H-indazol-7-ylmethyl)-1H-indazole-5-carboxylic acid;
- 1-(5-Fluoro-1-isobutyl-1H-indazol-7-ylmethyl)-1H-indazole-5-carboxylic acid;
- 1-(1-Isobutyl-5-trifluoromethyl-1H-indazol-7-ylmethyl)-1H-indazole-5-carboxylic acid;
- 1-(1-Isobutyl-5-trifluoromethoxy-1H-indazol-7-ylmethyl)-1H-indazole-5-carboxylic acid;
- 1-(5-Bromo-1-isopropyl-1H-indazol-7-ylmethyl)-1H-indazole-5-carboxylic acid;
- 1-[5-Bromo-1-(2-ethyl-butyl)-1H-indazol-7-ylmethyl]-1H-indazole-5-carboxylic acid;
- 1-[5-Chloro-1-(2-propyl)-1H-indazol-7-ylmethyl]-1H-indazole-5-carboxylic acid;
- 1-(5-Chloro-1-isobutyl-1H-indazol-7-ylmethyl)-1H-pyrazolo[3,4-b]pyridine-5-carboxylic acid;
- 1-(5-Chloro-1-isobutyl-1H-indazol-7-ylmethyl)-1H-benzoimidazole-5-carboxylic acid;
- 3-(5-Chloro-1-isobutyl-1H-indazol-7-ylmethyl)-3H-imidazo[4,5-b]pyridine-6-carboxylic acid;
- 1-(5-Chloro-1-isobutyl-1H-indazol-7-ylmethyl)-1H-pyrrolo[2,3-b]pyridine-5-carboxylic acid;
- 1-(5-Bromo-1-isobutyl-1H-indazol-7-ylmethyl)-3-methyl-1H-indazole-5-carboxylic acid;
- 1-(5-Bromo-1-isobutyl-1H-indazol-7-ylmethyl)-3-methyl-1H-pyrazolo[3,4-b]pyridine-5-carboxylic HCl salt;
- 1-(1-Isobutyl-5-trifluoromethyl-1H-indazol-7-ylmethyl)-1H-benzoimidazole-5-carboxylic acid;
- 1-(1-Isobutyl-5-trifluoromethoxy-1H-indazol-7-ylmethyl)-1H-benzoimidazole-5-carboxylic acid;
- 3-[(5-Chloro-1-isobutyl-indazol-7-yl)methyl]imidazo[1,5-a]pyridine-7-carboxylic acid;
- 1-(5-Chloro-1-isobutyl-1H-indazol-7-ylmethyl)-2-oxo-2,3-dihydro-1H-indole-5-carboxylic acid;
- 3-Amino-1-[(5-chloro-1-isobutyl-indazol-7-yl)methyl]indazole-5-carboxylic acid;
- 1-[(5-Chloro-1-isobutyl-indazol-7-yl)methyl]-3-(methylamino)indazole-5-carboxylic acid;

or a pharmaceutically acceptable salt thereof.

16. A method of treating a patient suffering from a condition selected from the group consisting of inflammatory pain, neuropathic pain, visceral pain, and fibrosis, the method comprises administering to said patient an effective amount of a compound of claim 1.

17. A pharmaceutical composition comprising a compound of claim 1 and one or more pharmaceutically acceptable excipients.

* * * * *